(12) United States Patent
Starck et al.

(10) Patent No.: US 6,602,867 B1
(45) Date of Patent: Aug. 5, 2003

(54) TRIAZOLE COMPOUNDS WITH DOPAMINE-D3-RECEPTOR AFFINITY

(75) Inventors: Dorothea Starck, Ludwigshafen (DE); Hans-Jörg Treiber, Brühl (DE); Liliane Unger, Ludwigshafen (DE); Barbara Neumann-Schultz, Ladenburg (DE); Kai Blumbach, Dettelbach (DE); Dietmar Schöbel, Mannheim (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/889,161

(22) PCT Filed: Jan. 12, 2000

(86) PCT No.: PCT/EP00/00177

§ 371 (c)(1), (2), (4) Date: Jul. 11, 2001

(87) PCT Pub. No.: WO00/42036

PCT Pub. Date: Jul. 20, 2000

(30) Foreign Application Priority Data

Jan. 12, 1999 (DE) .......................... 199 00 811

(51) Int. Cl.⁷ .................. C07D 401/12; C07D 401/14; C07D 413/14; A61K 31/41; A61P 25/16

(52) U.S. Cl. ................. 514/217.07; 546/142; 546/141; 546/145; 546/148; 514/309; 514/235.2; 514/307; 514/253.05; 544/125; 544/363; 540/597

(58) Field of Search ............... 546/142, 141, 546/145, 148; 514/309, 235.2, 307, 253.05, 217.07; 544/125, 363; 540/597

(56) References Cited

U.S. PATENT DOCUMENTS

| | | | |
|---|---|---|---|
| 4,338,453 A | 7/1982 | Gall | 548/263 |
| 4,408,049 A | 10/1983 | Gall | 544/360 |
| 4,577,020 A | 3/1986 | Gall | 544/366 |
| 4,886,805 A | 12/1989 | Bru-Magniez et al. | 514/253 |
| 5,387,591 A | 2/1995 | Lavielle et al. | 514/307 |
| 5,407,946 A | 4/1995 | Lavielle et al. | 514/314 |
| 5,663,191 A | 9/1997 | Lavielle et al. | 514/411 |
| 5,723,484 A | 3/1998 | Lavielle et al. | 514/410 |
| 5,872,119 A | 2/1999 | Wermuth et al. | 514/254 |
| 5,985,895 A | 11/1999 | Wermuth et al. | 514/317 |

FOREIGN PATENT DOCUMENTS

| | | |
|---|---|---|
| CA | 2195243 | 2/1996 |
| CA | 2242015 | 12/1998 |
| DE | 44 25 144 | 1/1996 |
| WO | WO 92/20655 | 11/1992 |
| WO | WO 93/08799 | 5/1993 |
| WO | WO 94/25013 | 11/1994 |
| WO | WO 96/30333 | 10/1996 |
| WO | WO 96/31512 | 10/1996 |
| WO | WO 97/10210 | 3/1997 |
| WO | WO 97/17326 | 5/1997 |
| WO | WO 97/25324 | 7/1997 |
| WO | WO 97/40015 | 10/1997 |
| WO | WO 97/43262 | 11/1997 |
| WO | WO 97/47602 | 12/1997 |
| WO | WO 98/06699 | 2/1998 |
| WO | WO 98/24791 | 6/1998 |
| WO | WO 98/49145 | 11/1998 |
| WO | WO 98/50363 | 11/1998 |
| WO | WO 98/50364 | 11/1998 |
| WO | WO 98/51671 | 11/1998 |
| WO | WO 99/02503 | 1/1999 |

OTHER PUBLICATIONS

Sokoloff et al. "Molecular Cloning and Characterization of a novel dopamine receptor ($D_3$) as a target for neuroleptics" Nature vol. 347 (1990) pps 146–151.

Sokoloff et al. "Localization and Function of the $D_3$ Dopamine Receptor" Arzneim–Forsch/Drug Res. vol. 42 No. 1(1992) pp. 224–230.

Dooley et al. "Pramipexole—A Review of it Use in the Management of Early and Advanced Parkinson's Disease" Drug & Aging vol. 12 No. 6 (1998) pp. 496–514.

Schwartz et al. "The Dopamine $D_3$ Receptor as a Targe for Anti Psychotics" Novel Antipsychotic Drugs (1992) pp. 135–144.

Czarnocka–Janowicz et al. "Synthesis and Pharmacological activity of 5–substituteds–s–triazole–3–thiols" Pharmazie No. 46 (1991) pp. 109–112.

Dubuffet et al. "Novel Benzopyrano[3,4–c]pyrrole Derivatives As Potent and selective dopamine $D_3$ Receptor Antagonists" Biororganic Medicinal Chemistry Letters No. 9 (1999) pp. 2059–2064.

*Primary Examiner*—Richard L. Raymond
*Assistant Examiner*—Hong Liu
(74) *Attorney, Agent, or Firm*—Keil & Weinkauf

(57) ABSTRACT

Triazole compounds of the following formula

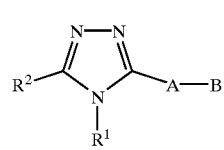

(I)

where $R^1$, $R^2$, A and B have the meanings given in the description are described. The compounds according to the invention possess a high affinity for the dopamine $D_3$ receptor and can therefore be used for treating diseases which respond to the influence of dopamine $D_3$ ligands.

18 Claims, No Drawings

TRIAZOLE COMPOUNDS WITH DOPAMINE-D3-RECEPTOR AFFINITY

The invention relates to triazole compounds and to the use of these compounds. These compounds possess valuable therapeutic properties and can be used for treating diseases which respond to the influence of dopamine $D_3$ receptor ligands.

Compounds of the type which is under discussion here and which possess physiological activity are already known. Thus, WO 94/25013; 96/02520; 97/43262; 97/47602; 98/06699; 98/49145; 98/50363; 98/50364 and 98/51671 describe compounds which act on the dopamine receptors. DE 44 25 144 A, WO 96/30333, WO 97/25324, WO 97/40015, WO 97/47602, WO 97/17326, EP 887 350, EP 779 284 A and Bioorg. & Med. Chem. Letters 9 (1999) 2059–2064 disclose further compounds which possess activity as dopamine $D_3$ receptor ligands. U.S. Pat. Nos. 4,338,453; 4,408,049 and 4,577,020 disclose triazole compounds which possess antiallergic or antipsychotic activity. WO 93/08799 and WO 94/25013 describe compounds of the type which is under discussion here and which constitute endothelin receptor antagonists. Additional triazole compounds, which inhibit blood platelet aggregation and which have a hypotensive effect are described in *Pharmazie* 46 (1991), 109–112. Further triazole compounds which possess physiological activity are disclosed in EP 691 342, EP 556 119, WO 97/10210, WO 98/24791, WO 96/31512 and WO 92/20655.

Neurons obtain their information by way of G protein-coupled receptors, inter alia. There are a large number of substances which exert their effect by way of these receptors. One of them is dopamine.

A number of facts about the presence of dopamine, and its physiological function as a neuron transmitter, are known with certainty. Disturbances of the dopaminergic transmitter system result in diseases such as schizophrenia, depression and Parkinson's disease. These, and other, diseases are treated with drugs which interact with the dopamine receptors.

By 1990, two subtypes of dopamine receptor had been clearly defined pharmacologically, namely the $D_1$ and $D_2$ receptors.

More recently, a third subtype has been found, namely the $D_3$ receptor, which appears to mediate some of the effects of the antipsychotic and anti-Parkinson agents (J. C. Schwartz et al., The Dopamine $D_3$ Receptor as a Target for Antipsychotics, in Novel Antipsychotic Drugs, H. Y. Meltzer, Ed. Raven Press, New York 1992, pages 135–144; M. Dooley et al., Drugs and Aging 1998, 12, 495–514).

Since $D_3$ receptors are chiefly expressed in the limbic system, it is assumed that while a selective $D_3$ ligand would probably have the properties of known antipsychotic agents, it would not have their dopamine $D_3$ receptor-mediated neurological side-effects (P. Sokoloff et al., Localization and Function of the $D_3$ Dopamine Receptor, *Arzneim. Forsch./Drug Res.* 42(1), 224 (1992); P. Sokoloff et al. Molecular Cloning and Characterization of a Novel Dopamine Receptor ($D_3$) as a Target for Neuroleptics, *Nature*, 347, 146 (1990)).

Surprisingly, it has now been found that certain triazole compounds exhibit a high affinity for the dopamine $D_3$ receptor and a low affinity for the $D_2$ receptor. These compounds are consequently selective $D_3$ ligands.

The present invention relates, therefore, to the compounds of the formula I:

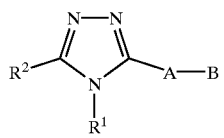

where
- $R^1$ is H, $C_1$–$C_6$-alkyl, which may be substituted by OH, $OC_1$–$C_6$-alkyl, halogen or phenyl, $C_3$–$C_6$-cycloalkyl or phenyl;
- $R^2$ is H, $C_1$–$C_6$-alkyl, which may be substituted by OH, $OC_1$–$C_6$-alkyl, halogen or phenyl, $C_1$–$C_6$-alkoxy, $C_1$–$C_6$-alkylthio, $C_2$–$C_6$-alkenyl, $C_2$–$C_6$-alkynyl, $C_3$–$C_6$-cycloalkyl, halogen, CN, $COOR^3$, $CONR^3R^4$, $NR^3R^4$, $SO_2R^3$, $SO_2NR^3R^4$, or an aromatic radical which is selected from phenyl, naphthyl and a 5- or 6-membered heterocyclic radical having 1, 2, 3 or 4 heteroatoms which are selected, independently of each other, from O, N and S, with it being possible for the aromatic radical to have one or two substituents which are selected, independently of each other, from $C_1$–$C_6$-alkyl, which may be substituted by OH, $OC_1$–$C_6$-alkyl, halogen or phenyl, $C_1$–$C_6$-alkoxy, $C_2$–$C_6$-alkenyl, $C_2$–$C_6$-alkynyl, $C_3$–$C_6$-cycloalkyl, halogen, CN, $COR^3$, $NR^3R^4$, $NO_2$, $SO_2R^3$, $SO_2NR^3R^4$ and phenyl which may be substituted by one or two radicals which are selected, independently of each other, from $C_1$–$C_6$-alkyl, $C_1$–$C_6$-alkoxy, $NR^3R^4$, CN, $CF_3$, $CHF_2$ or halogen;
- $R^3$ and $R^4$ are, independently of each other, H, $C_1$–$C_6$-alkyl, which may be substituted by OH, $OC_1$–$C_6$-alkyl, halogen or phenyl, or phenyl;
- A is $C_4$–$C_{10}$-alkylene or $C_3$–$C_{10}$-alkylene which comprises at least one group Z which is selected from O, S, $CONR^3$, COO, CO, $C_3$–$C_6$-cycloalkyl and a double or triple bond;
- B is a radical of the following formula:

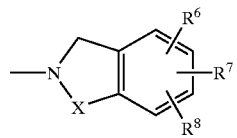

where
X is $CH_2$ or $CH_2CH_2$;
$R^6$, $R^7$ and $R^8$ are, independently of each other, selected from H, $C_1$–$C_6$-alkyl, which may be substituted by OH, $OC_1$–$C_6$-alkyl, which may be substituted by amino, mono- or di-$C_1$–$C_4$-alkylamino; $C_1$–$C_6$-alkylthio, halogen or phenyl; OH, $C_1$–$C_6$-alkoxy, $OCF_3$, $OSO_2CF_3$, SH, $C_1$–$C_6$-alkylthio, $C_2$–$C_6$-alkenyl, $C_2$–$C_6$-alkynyl, halogen, CN, $NO_2$, $CO_2R^3$, $SO_2R^3$, $SO_2NR^3R^4$, where $R^3$ and $R^4$ have the abovementioned meanings and may also form together with the N atom to which they are bonded a saturated or unsaturated heterocycle with 5 to 7 ring atoms and 1 or 2 N and/or O heteroatoms, $CONR^3R^4$, $NHSO_2R^3$, $NR^3R^4$, a 5- or 6-membered carbocyclic, aromatic or nonaromatic ring and a 5- or 6-membered heterocyclic, aromatic or nonaromatic ring with 1 or 2 heteroatoms which are selected, independently of each other, from O, N and S, with the carbocyclic or heterocyclic ring being able to have one or two substituents which are selected, independently of each other, from $C_1$–$C_6$-alkyl, phenyl, phenoxy, halogen, $C_1$–$C_6$-alkoxy, OH, $NO_2$, $CF_3$ and $CHF_2$, and with two of the substituents $R^6$, $R^7$ and $R^8$ being able to form, together with the carbon atoms of the phenyl ring to which they are bonded, a phenyl, cyclopentyl or cyclohexyl ring which is fused to the phenyl ring with the possibility for one or two of the CH or $CH_2$ groups in the fused ring being replaced by a nitrogen atom, a NH or a N—($C_1$–$C_6$-alkyl) group;
and the salts thereof with physiologically tolerated acids.

The compounds according to the invention are selective dopamine $D_3$ receptor ligands which act in the limbic system in a regioselective manner and which, as a result of their low affinity for the $D_2$ receptor, have fewer side-effects than do the classic neuroleptic agents, which are $D_2$ receptor antagonists. The compounds can therefore be used for treating diseases which respond to dopamine $D_3$ ligands, i.e. they are effective for treating those diseases in which affecting (modulating) the dopamine $D_3$ receptors leads to an improvement in the clinical picture or to the disease being cured. Examples of such diseases are diseases of the cardiovascular system and the kidneys, diseases of the central nervous system, in particular schizophrenia, affective disorders, neurotic stress and somatoform disorders, psychoses, Parkinsonism, attention deficit disorders, hyperactivity in children, epilepsy, amnesic and cognitive disorders such as learning and memory impairment (impaired cognitive function), anxiety states, dementia, delirium, personality disorders, sleep disturbances (for example restless legs syndrome), disorders of the sex life (male impotence), eating disorders and addictive disorders. Moreover they are useful in the treatment of stroke.

Addictive disorders include the psychological disorders and behavioral disturbances caused by the abuse of psychotropic substances such as pharmaceuticals or drugs, and other addictive disorders such as, for example, compulsive gambling (impulse control disorders not elsewhere classified). Addictive substances are, for example: opioids (for example morphine, heroin, codeine); cocaine; nicotine; alcohol; substances which interact with the GABA chloride channel complex, sedatives, hypnotics or tranquilizers, for example benzodiazepines; LSD; cannabinoids; psychomotor stimulants such as 3,4-methylenedioxy-N-methyl-amphetamine (ecstasy); amphetamine and amphetamine-like substances such as methylphenidate or other stimulants including caffeine. Addictive substances of particular concern are opioids, cocaine, amphetamine or amphetamine-like substances, nicotine and alcohol.

The compounds according to the invention are preferably used for treating affective disorders; neurotic, stress and somatoform disorders and psychoses, e.g. schizophrenia.

Within the context of the present invention, the following expressions have the meanings given in conjunction with them:

Alkyl (also in radicals such as alkoxy, alkylthio, alkylamino etc.) is a straight-chain or branched alkyl group having from 1 to 6 carbon atoms and, in particular from 1 to 4 carbon atoms. The alkyl group can have one or more substituents which are selected, independently of each other, from OH, $OC_1$–$C_6$-alkyl, halogen or phenyl. In the case of a halogen substituent, the alkyl group can, in particular, encompass, 1, 2, 3 or 4 halogen atoms which can be located on one or more C atoms, preferably in the α or ω position. $CF_3$, $CHF_2$, $CF_2Cl$ or $CH_2F$ are particularly preferred.

Examples of an alkyl group are methyl, ethyl, n-propyl, iso-propyl, n-butyl, iso-butyl, t-butyl, etc.

Cycloalkyl is, in particular, $C_3$–$C_6$-cycloalkyl, such as cyclopropyl, cyclobutyl, cyclopentyl and cyclohexyl.

Alkylene radicals are straight-chain or branched. If A does not have a group Z, A then comprises from 4 to 10 carbon atoms, preferably from 4 to 8 carbon atoms. The chain between the triazole nucleus and group B then has at least four carbon atoms. If A has at least one of said Z groups, A then comprises from 3 to 10 carbon atoms, preferably from 3 to 8 carbon atoms.

If the alkylene groups comprise at least one of the Z groups, this or these groups can then be arranged in the alkylene chain at an arbitrary site or in position 1 or 2 of the A group (seen from the triazole radical). The radicals $CONR^2$ and COO are preferably arranged such that the carbonyl group is in each case facing the triazole ring. Particular preference is given to the compounds of the formula I in which A is —Z—$C_3$–$C_6$-alkylene, in particular —Z—$CH_2CH_2CH_2$—, —Z—$CH_2CH_2CH_2CH_2$—, —Z—$CH_2CH$=$CHCH_2$—, —Z—$CH_2C(CH_3)$=$CHCH_2$—,

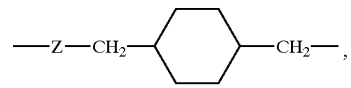

—Z—$CH_2CH(CH_3)CH_2$— or a linear —Z—$C_7$–$C_{10}$-alkylene radical, with Z being bonded to the triazole ring. Z is preferably $CH_2$, O and, in particular, S. Preference is additionally given to A being —$(CH_2)_4$—, —$(CH_2)_5$—, —$CH_2CH_2CH$=$CHCH_2$—,

—$CH_2CH_2C(CH_3)$=$CHCH_2$— or —$CH_2CH_2CH(CH_3)CH_2$—.

Halogen is F, Cl, Br or I, preferably F or Cl.

X is preferably —$CH_2$–$CH_2$—.

$R^1$ is preferably H, $C_1$–$C_6$-alkyl or $C_3$–$C_6$-cycloalkyl.

If $R^2$ is an aromatic radical, this radical is then preferably one of the following radicals:

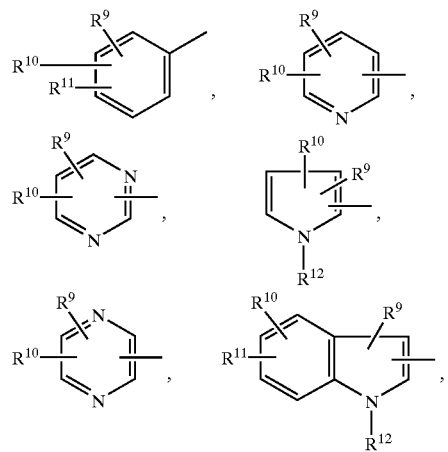

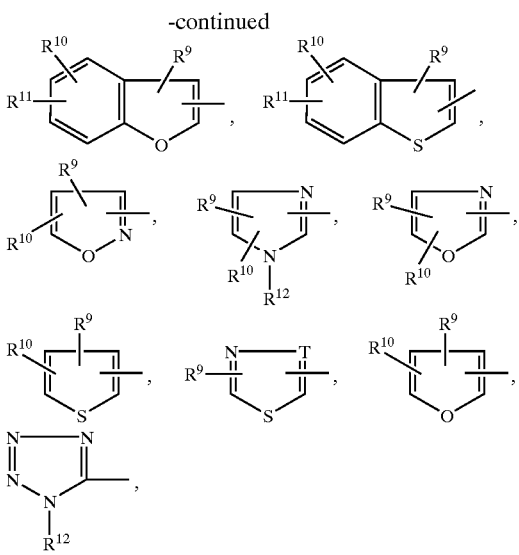

where
- $R^9$ to $R^{11}$ are H or the abovementioned substituents of the aromatic radical,
- $R^{12}$ is H, $C_1$–$C_6$-alkyl or phenyl, and T is N or CH.

If the phenyl radical is substituted, the substituents are preferably in the m position or the p position.

The aromatic radical is particularly preferably a group of the formula:

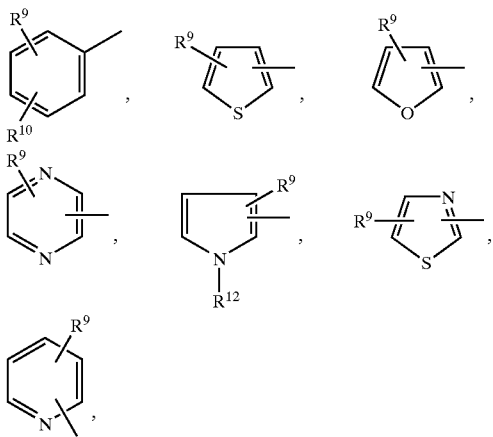

where $R^9$, $R^{10}$ and $R^{12}$ have the abovementioned meanings. The indicated phenyl, pyridine, thiazolyl and pyrrole radicals are particularly preferred.

The radicals $R^9$ to $R^{11}$ are preferably H, $C_1$–$C_6$-alkyl, $OR^3$, CN, phenyl, which may be substituted by $C_1$–$C_6$-alkyl, $C_1$–$C_6$-alkoxy or halogen, $CF_3$ and halogen, and are, in particular, H, $C_1$–$C_6$-alkyl, $OR^3$ and halogen. In this context, $R^3$ has the abovementioned meanings.

Particularly preferably, $R^2$ is H, $C_1$–$C_6$-alkyl, $NR^3R^4$ ($R^3$ and $R^4$ are, independently of each other, H or $C_1$–$C_6$-alkyl), phenyl or a 5-membered aromatic heterocyclic radical which has 1 or 2 heteroatoms which are independently selected from N, S and O. The heterocyclic radical is preferably a pyrrole radical or a pyridine radical.

A is preferably $C_4$–$C_{10}$-alkylene or $C_3$–$C_{10}$-alkylene which comprises at least one group Z which is selected from O, S, COO, CO, a double bond and cyclohexyl.

Preferably, at least one of the radicals $R^6$, $R^7$ and $R^8$ is H.

The radicals $R^6$, $R^7$ and $R^8$ are preferably, and independently of each other, selected from H, $C_1$–$C_6$-alkyl, OH, $C_1$–$C_6$-alkoxy, $C_1$–$C_6$-alkylthio-$C_1$–$C_6$-alkyl, halogen, CN, $NO_2$, $SO_2R^3$, $SO_2NR^3R^4$ and $CONR^3R^4$. Particularly preferably, the fused phenyl group has one or two substituents, i.e. one or two of the radicals $R^6$, $R^7$ and $R^8$ is/are $C_1$–$C_6$-alkyl, halogen, CN, $NO_2$, $SO_2R^3$ and, in particular, $SO_2NR^3R^4$, where $R^3$ and $R^4$, together with the N atom to which they are attached, can also be a 5-, 6- or 7-membered heterocycle, which may contain one or two additional heteroatoms being selected from N, O or S besides the nitrogen atom and which may be substituted, e.g. pyrrolidine, piperidine, morpholine or azepine.

If one of the radicals $R^6$, $R^7$ and $R^8$ is a 5- or 6-membered heterocyclic ring, this ring is then, for example, a pyrrolidine, piperidine, morpholine, pyridine, pyrimidine, triazine, pyrrole, thiophene or pyrazole radical, with a pyrrole, pyrrolidine, pyrazole or thienyl radical being preferred.

If one of the radicals $R^6$, $R^7$ and $R^8$ is a carbocyclic radical, this radical is then, in particular, a phenyl, cyclopentyl or cyclohexyl radical.

Particular preference is given to the compounds of formula I where
- $R^1$ is H, $C_1$–$C_6$-alkyl or phenyl,
- $R^2$ is H, $C_1$–$C_6$-alkyl, phenyl, thienyl, furanyl, pyridyl, pyrrolyl, thiazolyl or pyrazinyl,
- A is —$SC_3$–$C_{10}$-alkylene which can comprise a double bond, and
- $R^6$, $R^7$ and $R^8$ are selected from H, $C_1$–$C_6$-alkyl, $C_1$–$C_6$-alkoxy, halogen, $SO_2NR^3R^4$, CN, $NO_2$, $CF_3$, $CONR^3R^4$, $CHF_2$, $OSO_2CF_3$, $OCF_3$ and $NHSO_2$–$C_1$–$C_6$-alkyl.

In here X is especially $CH_2CH_2$.

The invention also encompasses the acid addition salts of the compounds of the formula I with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid or benzoic acid. Other acids which can be used are described in Fortschritte der Arzneimittelforschung [Advances in pharmaceutical research], Volume 10, pages 224 ff., Birkhäuser Verlag, Basle and Stuttgart, 1966.

The compounds of the formula I can exhibit one or more centers of asymmetry. The invention therefore includes not only the racemates but also the relevant enantiomers and diastereomers. The respective tautomeric forms are also included in the invention.

The process for preparing the compounds of the formula I consist in a) reacting a compound of the formula (II)

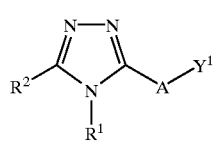

where $Y^1$ is a customary leaving group, such as Hal, alkylsulfonyloxy, arylsulfonyloxy, etc., with a compound of the formula (III)

HB     (III);

or b) reacting a compound of the formula (IV)

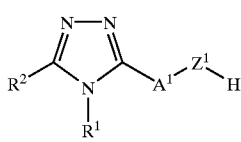
(IV)

where $Z^1$ is O or S, and $A^1$ is $C_1$–$C_{10}$-alkylene or a bond, with a compound of the formula (V)

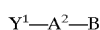
$Y^1$—$A^2$—B  (V)

where $Y^1$ has the abovementioned meaning and $A^2$ is $C_2$–$C_{10}$-alkylene, with $A^1$ and $A^2$ together having from 3 to 10 C atoms and $A^1$ and/or $A^2$ where appropriate comprising at least one group Z; or c) reacting a compound of the formula (VI)

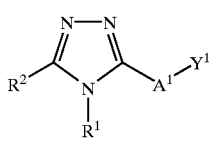
(VI)

where $Y^1$ and $A^1$ have the abovementioned meanings, with a compound of the formula (VII)

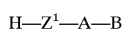
H—$Z^1$—A—B  (VII)

where $Z^1$ has the abovementioned meanings; or d) reversing the polarity of a compound of the formula (VIII)

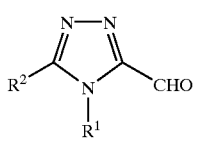
(VIII)

using reagents which are known from the literature, such as 1,3-propanedithiol, KCN/water, TMSCN (trimethylsilyl cyanide) or KCN/morpholine, as described, for example, in Albright *Tetrahedron*, 1983, 39, 3207 or
D. Seebach *Synthesis* 1969, 17 und 1979, 19 or
H. Stetter *Angew. Chem. Int. Ed.* 1976, 15, 639 or
van Niel et al. *Tetrahedron* 1989, 45, 7643
Martin et al. *Synthesis* 1979, 633, to give the products (VIIIa) (using 1,3-propanedithiol by way of example)

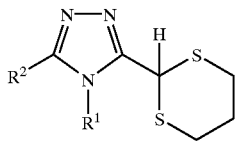
(VIIIa)

and then chain-elongating with compounds of the formula (IX)

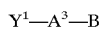
$Y^1$—$A^3$—B  (IX)

where $Y^1$ has the abovementioned meaning and $A^3$ is $C_3$–$C_9$-alkylene which can contain a group Z, with compounds of the formula (Ia)

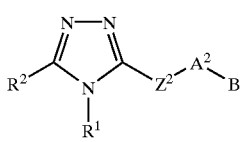
(Ia)

where $Z^2$ is CO or a methylene group, and $Z^2$ and $A^2$ have together from 4 to 10 C atoms, being obtained after deprotecting or reducing, or e) reacting a compound of the formula (VIII) with a compound of the formula (X)

$Y^2$—A—B  (X)

where $Y^2$ is a phosphorane or a phosphonic ester, in analogy with customary methods, as described, for example, in Houben Weyl *"Handbuch der Organischen Chemie"* [Textbook of Organic Chemistry], 4th Edition, Thieme Verlag Stuttgart, Volume V/1b p. 383 ff, or Vol. V/1c p. 575 ff, or f) reacting a compound of the formula (XI)

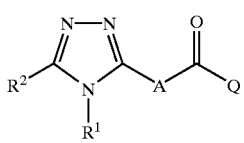
(XI)

where Q is H or OH, with a compound of the formula III under reductive conditions in analogy with methods known from the literature, for example as described in *J. Org. Chem.* 1986, 50, 1927; or WO 92/20655.

The process for preparing a compound of the formula I where A comprises the groups COO or $CONR^3$ consists in reacting a compound of the formula (XII)

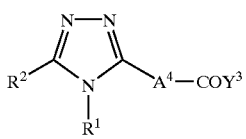
(XII)

where $Y^3$ is OH, $OC_1$–$C_4$-alkyl, Cl or, together with CO, an activated carboxyl group, and $A^4$ is $C_0$–$C_9$-alkylene, with a compound of the formula (XIII)

B—A—$Z^3$  (XIII)

where $Z^3$ is OH or $NHR^3$.

Compounds of the formula B—H can be prepared as described, for example, in

Synth. Commun. 1984, 14, 1221;
S. Smith et al., *Bioorg. Med. Chem. Lett.* 1998, 8, 2859;
WO 97/47602 or WO 920655, or
*J. Med. Chem.* 1987, 30, 2111 and 2208 and 1999, 42, 118.

The compounds of the formula (IV) type are either known or can be prepared using known methods, as described, for example, in A. R. Katritzky, C. W. Rees (ed.) "Comprehensive Heterocyclic Chemistry", Pergamon Press, or "The Chemistry of Heterocyclic Compounds" J. Wiley & Sons Inc. NY and the literature which is cited therein, or in S.

Kubota et al. *Chem. Pharm. Bull.* 1975, 23, 955 or Vosilevskii et al. *Izv. Akad. Nauk. SSSR Ser. Khim.* 1975, 23, 955.

In the above formulae, $R^1$, $R^2$, $R^6$, $R^7$, $R^8$, A, B and X have the meanings given in connection with formula I.

The compounds according to the invention, and the starting materials and the intermediates, can also be prepared in analogy with the methods which are described in the patent publications which were mentioned at the outset.

The above-described reactions are generally effected in a solvent at temperatures of between room temperature and the boiling temperature of the solvent employed. Examples of solvents which can be used are esters, such as ethyl acetate, ethers, such as diethyl ether or tetrahydrofuran, dimethylformamide, dimethyl sulfoxide, dimethoxyethane, toluene, xylene, acetonitrile, ketones, such as acetone or methyl ethyl ketone, or alcohols, such as ethanol or butanol.

If desired, the reactions can be carried out in the presence of an acid-binding agent. Suitable acid-binding agents are inorganic bases, such as sodium carbonate or potassium carbonate, or sodium hydrogencarbonate or potassium hydrogencarbonate, sodium methoxide, sodium ethoxide, sodium hydride, or organometallic compounds, such as butyl lithium or alkyl magnesium compounds, or organic bases, such as triethylamine or pyridine. The latter can also simultaneously serve as the solvent.

Process (f) is effected under reducing conditions, e.g. using sodium borohydride, sodium cyanoborohydride or triacetoxy borohydride, where appropriate in an acid medium or in the presence of a Lewis acid, such as zinc chloride, or by way of catalytic hydrogenation.

The crude product is isolated in a customary manner, for example by means of filtering, distilling off the solvent or extracting from the reaction mixture, etc. The resulting compounds can be purified in a customary manner, for example by recrystallization from a solvent, by chromatography or by converting into an acid addition compound.

The acid addition salts are prepared in a customary manner by mixing the free base with the corresponding acid, where appropriate in solution in an organic solvent, for example a lower alcohol, such as methanol, ethanol or propanol, an ether, such as methyl tert-butyl ether, a ketone, such as acetone or methyl ethyl ketone, or an ester, such as ethyl acetate.

For treating the abovementioned diseases, the compounds according to the invention are administered orally or parenterally (subcutaneously, intravenously, intramuscularly or intraperitoneally) in a customary manner. The administration can also be effected through the nasopharyngeal space using vapors or sprays.

The dosage depends on the age, condition and weight of the patient and on the type of administration. As a rule, the daily dose of active compound is from about 10 to 1000 mg per patient and day when administered orally and from about 1 to above 500 mg per patient and day when administered parenterally.

The invention also relates to pharmaceuticals which comprise the compounds according to the invention. In the customary pharmacological administration forms, these pharmaceuticals are present in solid or liquid form, for example as tablets, film tablets, capsules, powders, granules, sugar-coated tablets, suppositories, solutions or sprays. In this context, the active compounds can be worked up together with the customary pharmacological auxiliary substances, such as tablet binders, fillers, preservatives, tablet disintegrants, flow-regulating agents, plasticizers, wetting agents, dispersants, emulsifiers, solvents, retarding agents, antioxidants and/or propellent gases (cf. H. Sucker et al., Pharmazeutische Technologie, Thieme-Verlag, Stuttgart, 1978). The resulting administration forms normally comprise the active compound in a quantity of from 1 to 99% by weight.

The following examples serve to explain the invention without limiting it.

EXAMPLE 1

6,7-Dimethoxy-2-{3-[(4-methyl-5-phenyl-4H-1,2,4-triazol-3-yl)-sulfanyl]propyl}-1,2,3,4-tetrahydroisoquinoline 1A Preparation of the Starting Materials 2-(3-Chloropropyl)-6,7-dimethoxy-1,2,3,4-tetrahydroisoquinoline 7.2 g (37 mmol) of 6,7-dimethoxy-1,2,3,4-tetrahydroisoquinoline were heated together with 4.05 ml (40 mmol) of 1-bromo-3-chloropropane, 11.3 g (81 mmol) of potassium carbonate and 610 mg (40 mmol) of sodium iodide in 250 ml of acetonitrile with stirring at 70° C. for four hours. After the reaction was complete, the solvent was distilled off, and the residue was taken up in water and extracted with methylene chloride. The combined organic phases were dried and concentrated, and the crude product was purified by chromatography on silica gel (mobile phase: methylene chloride/methanol=9/1). 4.8 g (45% of theory) of a yellowish oil were obtained.

$^1$H-NMR (CDCl$_3$): δ=2.0 (m, 2H); 2.6–2.8 (m, 6H); 3.5 (s, 2H); 3.6 (t, 2H); 3.8 (2s, 6H); 6.5 (s, 1H); 5.6 (s, 1H). $C_{14}H_{20}ClNO_2$ (269).

1B Preparation of the Final Product 380 mg (1.7 mmol) of 3-mercapto-4-methyl-5-phenyl-1,2,4(4H)-triazole were heated with 450 mg (1.7 mmol) of the chlorinated base 1A and 40 mg (1.7 mmol) of lithium hydroxide in 5 ml of DMF while stirring at 100° C. for five hours. Workup entailed addition of 50 ml of water, extraction several times with methyl tert-butyl ether, drying of the combined organic phases, evaporation and purification by chromatography on silica gel (mobile phase: methylene chloride/2–5% methanol).

Yield: 0.2 g (49% of theory); $^1$H-NMR (CDCl$_3$): δ=2.1 (q, 2H); 2.6 (m, 2H); 2.7 (m, 2H); 2.8 (m, 2H); 3.3 (t, 2H); 3.5 (m, 2H); 3.6 (s, 3H); 3.8 (2s, 6H); 6.3 (s, 1H); 6.5 (s, 1H); 7.5 (m, 3H); 7.8 (m, 2H).

The title compound was obtained by treatment with ethereal hydrochloric acid $C_{23}H_{28}N_4O_2S \times HCl$ Melting point: 180–183° C.

EXAMPLE 2

6-Methoxy-2-{3-[(4-methyl-5-pyrrol-2-yl-4H-1,2,4-triazol-3-yl)-sulfanyl]propyl}-1,2,3,4-tetrahydroisoquinoline 2A Preparation of the Starting Compound 2-(3-Chloropropyl)-6-methoxy-1,2,3,4-tetrahydroisoquinoline The above substance was prepared using 6-methoxy-1,2,3,4-tetrahydroisoquinoline in a manner analogous to 1A.

$^1$H-NMR (CDCl$_3$): δ=2.0 (q, 2H); 2.5–2.6 (m, 4H); 2.9 (m, 2H); 3.5 (s, 2H); 3.6 (m, 2H); 3.8 (s, 3H); 6.6 (d, 1H); 6.7 (dd, 1H); 6.9 (d, 1H).

2B Preparation of the Final Product

Preparation took place in analogy to Example 1 by reacting the chlorinated base prepared in 2A with 3-mercapto-4-methyl-5-(2-pyrrolyl)-1,2,4(4H)-triazole.

Yield: 52% of theory. $C_{20}H_{25}N_5OS$ (383.5); Melting point: 179–181° C.

EXAMPLE 3

2-{3-[(4-Methyl-5-phenyl-4H-1,2,4-triazol-3-yl)sulfanyl]propyl}-6-methoxy-1,2,3,4-tetrahydroisoquinoline 3A Preparation of the Starting Material 3-(3-Chloropropylmercapto)-4-methyl-5-phenyl-1,2,4(4H)-triazole A suspension of 2.6 g (16.5 mmol) of 1-bromo-3-chloropropane, 0.22 g (1.5 mmol) of sodium iodide, 2.7 g (15 mmol) of 3-mercapto-4-methyl-5-phenyl-1,2,4(4H)-triazole and 2.1 g (15 mmol) of potassium carbonate in 70 ml of ethanol were heated to boiling for one hour. After filtration hot, the filtrate was concentrated, taken up in water and extracted with dichloromethane. The combined orgainc phases were dried, filtered and concentrated, and the residue was chromatographed (mobile phase: methylene chloride/2% methanol).

Yield: 1.35 g (34% of theory) of white solid; $^1$H-NMR (CDCl$_3$): δ=2.3 (q, 2H); 3.4 (t, 2H); 3.6 (s, 3H); 3.7 (t, 2H); 7.5–7.7 (m, 5H). $C_{12}H_{14}ClN_3S$ (267.8); Melting point: 137–141° C.

3B Preparation of the Final Product 0.7 g (2.5 mmol) of Compound 3A described above was stirred with 0.6 g (2.5 mmol) of 6-methoxy-1,2,3,4-tetrahydroisoquinoline oxalic acid salt in the presence of 1.1 ml (7.5 mmol) of triethylamine and catalytic amounts of sodium iodide in 6 ml of butanol at 120° C. for four hours. After the reaction was complete it was worked up by extraction with water and methyl tert-butyl ether, drying over sodium sulfate and concentrating, and the crude product was chromatographed on silica gel (mobile phase: methylene chloride with 0–3% methanol). 110 mg of a white solid were isolated.

$C_{22}H_{26}N_4OS$ (394.5) MS (m/z): 395 [M]$^+$.

EXAMPLE 4

2-{3-[(4-Methyl-5-phenyl-4H-1,2,4-triazol-3-yl)sulfanyl]propyl}-7-(piperidin-1-ylsulfonyl)-1,2,3,4-tetrahydroisoquinoline 4A Preparation of N-Acetyl-7-(piperidin-1-ylsulfonyl)-1,2,3,4-tetrahydroisoquinoline 21.1 g (77 mmol) of 2-acetyl-1,2,3,4-tetrahydroisoquinoline-7-sulfonyl chloride (prepared as described in G. Grunewald et al. J. Med. Chem 1999, 42, 118–134) in 50 ml of THF were added dropwise to a solution of 6.0 g (70 mmol) of piperidine and 10.9 g (84 mmol) of diisopropylethylamine in 230 ml of THF, and the mixture was heated under reflux for two hours. After the reaction was complete, the solvent was removed in vacuo, the residue was taken up in dichloromethane/water and, after making alkaline with 10% strength sodium hydroxide solution and separating the phases, the organic phase was dried over sodium sulfate. The crude product remaining after filtration and removal of the solvent was purified by column chromatography on silica gel (mobile phase: methylene chloride with 3% methanol).

Yield: 18.6 g (57.6 mmol); 82%; Melting point:171–174° C.

4B 7-(Piperidin-1-ylsulfonyl)-1,2,3,4-tetrahydroisoquinoline

The compound described above was heated to boiling with 50% concentrated hydrochloric acid for two hours. The product formed a white precipitate on cooling. The residue was isolated, washed with water, digested in diethyl ether and dried in vacuo.

Yield: 12.1 g (38.2 mmol) 56% of theory.

4C 2-(3-Chloropropyl)-7-(piperidin-4-ylsulfonyl)-1,2,3,4-tetrahydroisoquinoline 12.1 g (38.2 mmol) of 7-(piperidin-1-ylsulfonyl)-1,2,3,4-tetra-hydroisoquinoline and 8.4 g (84 mmol) of triethylamine were dissolved in DMF at 40° C., 9.0 g (57.2 mmol) of 1-bromo-3-chloropropane were added dropwise, and the mixture was stirred at 50° C. for 7 h. For workup, the mixture was concentrated, and the residue was taken up in water and extracted with dichloromethane. Drying over sodium sulfate, filtration and removal of the solvent were followed by purification by chromatography (silica gel; mobile phase: methylene chloride with 3% methanol) to result in 11.7 g (323.7 mmol) of a yellowish oil.

Yield: 86% of theory.

4D Preparation of the Final Compound 10.0 g (28.0 mmol) of the chlorinated base 4C described above, 6.4 g (28 mmol) of 3-mercapto-4-methyl-5-phenyl-4H-1,2,4-triazole and 0.7 g (28.0 mmol) of lithium hydroxide were heated in 77 ml of DMF at 100° C. for three hours. After the reaction was complete, the solvent was removed, and the residue was mixed with water and extracted with ethyl acetate. The combined organic phases were dried over sodium sulfate, filtered and evaporated. Chromatography of the crude product (silica gel; mobile phase: methylene chloride with 0–5% methanol) afforded 3.9 g (7.5 mmol) of a white solid.

Yield: 27% of theory; $^1$H-NMR (CDCl$_3$): δ=1.4 (m, 2H); 1.7 (m, 4H); 2.1 (q, 2H); 2.7 (t, 2H); 2.8 (t, 2H); 3.0 (m, 6H); 3.35 (t, 2H); 3.6 (s, 3H); 3.7 (s, 2H); 7.2 (d, 1H); 7.4 (s, 1H); 7.5 (m, 4H); 7.7 (m, 2H). $C_{26}H_{33}N_5O_2S_2$ (511.7) MS (m/z): 512.3 [M+H]$^+$; Melting point: 105–108° C.

EXAMPLE 5

2-[4-(4-Methyl-5-phenyl-4H-1,2,4-triazol-3-yl)butyl]-7-(morpholin-4-ylsulfonyl)-1,2,3,4-tetrahydroisoquinoline Hydrochloride Preparation of the Starting Compound 5A N-Acetyl-7-(morpholin-4-ylsulfonyl)-1,2,3,4-tetrahydroisoquinoline was obtained as described in Example 4A by reacting morpholine with 2-acetyl-1,2,3,4-tetrahydroisoquinoline-7-sulfonyl chloride in the presence of diisopropylamine in THF and by heating with 50% concentrated hydrochloric acid and, after alkaline workup, converted into the corresponding 7-(morpholin-4-ylsulfonyl)-1,2,3,4-tetrahydroisoquinoline.

$C_{13}H_{18}N_2O_3S$ (282) MS (m/z): 283 [M+H]$^+$.

5B 2-(3-Chloropropyl)-7-(morpholin-4-ylsulfonyl)-1,2,3,4-tetrahydroisoquinoline 1.2 g (4.4 mmol) of 7-(morpholin-4-ylsulfonyl)-1,2,3,4-tetra-hydroisoquinoline and 1.0 g (10 mmol) of triethylamine were dissolved in DMF at 40° C., 1.1 g (6.6 mmol) of 1-bromo-3-chloropropane were added dropwise, and the mixture was stirred at 40° C. for 3 h. For workup, the mixture was concentrated, and the residue was taken up in water and extracted with methyl tert-butyl ether. Drying over sodium sulfate, filtration and removal of the solvent were followed by purification by chromatography (silica gel; mobile phase: methylene chloride with 2% methanol) to afford 0.7 g (2 mmol) of a pale oil.

Yield: 46% of theory. $^1$H-NMR (CDCl$_3$): δ=2.0 (q, 2H); 2.7 (t, 2H); 2.8 (t, 2H); 3.0 (m, 6H); 3.6–3.8 (m, 8H); 7.3 (d, 1H); 7.4 (s, 1H); 7.5 (d, 1H). $C_{16}H_{23}N_2O_3S$ (359).

Preparation of the Final Compound 280 mg (1 mmol) of 2-[4-methyl-5-phenyl-1,2,4-(4H)-triazol-3-yl]-1,3-dithiane (described in WO 9902503) were dissolved in 2.5 ml of dry THF and, at −70° C., with the addition of 0.15 g of sodium iodide, treated with 0.75 ml (1.2 mmol) of a 15% strength solution of butyllithium in n-hexane. After stirring at −70+ C. for 45 min, 0.37 g (1 mmol) of 2-[3-chloropropyl]-7-(morpholin-4-yl-sulfonyl)-1,2,3,4-tetrahydroisoquinoline 5B dissolved in THF was added dropwise. The mixture was then slowly warmed to room temperature and subsequently heated at 40° C. for 90 min in order to achieve complete conversion. Workup entailed addition to ice/water and extraction several times with methylene chloride. After drying and concentration, 0.5 g (82% of theory) of the substituted dithiane remained and was then hydrogenated with Raney nickel and hydrogen in tetrahydrofuran at 40° C. over the course of 3 hours. After removal of the catalyst, the residue was purified by chromatography (silica gel, methylene chloride with 5% methanol).

Yield: 120 mg (29% of theory); 1H-NMR (CDCl$_3$): δ=1.8 (m, 2H); 2.0 (q, 2H); 2.6 (m, 2H); 2.7 (t, 2H); 2.9 (t, 2H); 3.0 (m, 6H); 3.6 (s, 3H); 3.7 (m, 6H); 7.2 (d, 1H); 7.4 (s, 1H); 7.5 (m, 4H); 7.7 (m, 2H).

The title compound was obtained by adding ethereal HCl C$_{26}$H$_{33}$N$_5$O$_3$S.HCl (531.6); Melting point: 87–89° C.

The following were obtained in an analogous way:

EXAMPLE 6

1-(4-Methyl-5-phenyl-4H-1,2,4-triazol-3-yl)-4-(7-(piperidin-1-yl-sulfonyl)-1,2,3,4-tetrahydroisoquinolin-2-yl)butan-1-one

C$_{27}$H$_{33}$N$_5$O$_3$S (507.7) MS: 508.3 [M+H]$^+$.

EXAMPLE 7

2-{3-[(4-Methyl-5-phenyl-4H-1,2,4-triazol-3-yl)sulfanyl]propyl}-1,2,3,4-tetrahydroisoquinoline-7-carbonitrile C$_{22}$H$_{23}$N$_5$S (389.5); Melting point: 116–118° C.

EXAMPLE 8

5-[2-(Diethylammonio)ethoxy]-2-{3-[(4-methyl-5-phenyl-4H-1,2,4-triazol-3-yl)sulfanyl]propyl}-1,2,3,4-tetrahydroisoquinoline Dihydrochloride C$_{27}$H$_{37}$N$_5$OS.2HCl (552.6); Melting point: 110–112° C.

EXAMPLE 9

N-Benzyl-2-(3-{[4-methyl-5-(4-methyl-1,3-thiazol-5-yl)-4H-1,2,4-triazol-3-yl]sulfanyl}propyl)-1,2,3,4-tetrahydroisoquinoline-7-sulfonamide C$_{26}$H$_{30}$N$_6$O$_2$S$_3$ (554.8); Melting point: 67–70° C.

EXAMPLE 10

N-Benzyl-2-{3-[(4-methyl-5-pyridin-3-yl-4H-1,2,4-triazol-3-yl)-sulfanyl]propyl}-1,2,3,4-tetrahydroisoquinoline-7-sulfonamide C$_{27}$H$_{30}$N$_6$O$_2$S$_2$.2HCl (607.6); Melting point: 81–84° C.

EXAMPLE 11

5-Methoxy-2-{3-[(4-methyl-5-phenyl-4H-1,2,4-triazol-3-yl)-sulfanyl]propyl}-1,2,3,4-tetrahydroisoquinoline C$_{22}$H$_{26}$N$_4$OS (394.5); Melting point: 73–75° C.

EXAMPLE 12

2-{3-[(4-Methyl-5-phenyl-4H-1,2,4-triazol-3-yl)sulfanyl]propyl}-7-nitro-1,2,3,4-tetrahydroisoquinoline C$_{21}$H$_{24}$ClN$_5$O$_2$S (446); Melting point: 190–192° C.

EXAMPLE 13

2-{3-[(4-Methyl-5-phenyl-4H-1,2,4-triazol-3-yl)sulfanyl]propyl}-1,2,3,4-tetrahydroisoquinoline $^1$H-NMR (CDCl$_3$): δ=2.1 (q, 2H); 2.65 (t, 2H); 2.7 (t, 2H); 2.9 (t, 2H); 3.4 (t, 2H); 3.5 (s, 3H); 3.7 (s, 2H); 7.0 (m, 1H); 7.2 (m, 3H); 7.5 (m, 3H); 7.7 (m, 2H). C$_{21}$H$_{24}$N$_4$S (365.5).

EXAMPLE 14

2-(3-{[4-Methyl-5-(4-methyl-1,3-thiazol-5-yl)-4H-1,2,4-triazol-3-yl]sulfanyl}propyl)-1,2,3,4-tetrahydroisoquinoline $^1$H-NMR (CDCl$_3$): δ=2.1 (q, 2H); 2.55 (s, 3H); 2.7 (t, 2H); 2.75 (t, 2H); 2.9 (t, 2H); 3.4 (t, 2H); 3.5 (s, 3H); 3.65 (s, 2H); 7.0 (m, 1H); 7.1 (m, 3H); 8.9 (s, 1H). C$_{19}$H$_{23}$N$_5$S$_2$ (386.5).

EXAMPLE 15

2-{3-[(4-Methyl-5-pyridinium-3-yl-4H-1,2,4-triazol-3-yl)-sulfanyl]propyl}-1,2,3,4-tetrahydroisoquinoline Dihydrochloride C$_{20}$H$_{23}$N$_5$S.2HCl (438.4); Melting point: 87–89° C.

EXAMPLE 16

7-[(Dimethylamino)sulfonyl]-2-{3-[(4-methyl-5-phenyl-4H-1,2,4-triazol-3-yl)sulfanyl]propyl}-1,2,3,4-tetrahydroisoquinoline $^1$H-NMR (CDCl$_3$): δ=2.1 (q, 2H); 2.65 (m, 8H); 2.75 (t, 2H); 3.0 (t, 2H); 3.3 (t, 2H); 3.6 (s, 3H); 3.7 (s, 2H); 7.2 (d, 1H); 7.4–7.6 (m, 7H). C$_{23}$H$_{29}$N$_5$O$_2$S$_2$ (472.6).

EXAMPLE 17

7-[(Dimethylamino)sulfonyl]-2-(3-{[4-methyl-5-(4-methyl-1,3-thiazol-5-yl)-4H-1,2,4-triazol-3-yl]sulfanyl}propyl)-1,2,3,4-tetrahydroisoquinoline 1H-NMR (CDCl$_3$): δ=2.1 (q, 2H); 2.5 (s, 3H); 2.6–2.8 (m, 10H); 2.9 (m, 2H); 3.4 (t, 2H); 3.5 (s, 3H); 3.7 (s, 2H); 7.2 (m, 1H); 7.5 (m, 2H); 8.9 (s, 1H). C$_{21}$H$_{28}$N$_6$O$_2$S$_3$ (493.7).

EXAMPLE 18

Methyl 2-{3-[(4-Methyl-5-phenyl-4H-1,2,4-triazol-3-yl)-sulfanyl]propyl}-1,2,3,4-tetrahydroisoquinoline-7-carboxylate Oxalate C$_{23}$H$_{27}$N$_4$O$_2$S.C$_2$HO$_4$ (512.6); Melting point: 160–163° C.

EXAMPLE 20

2-(3-{[4-Methyl-5-(4-methyl-1,3-thiazol-5-yl)-4H-1,2,4-triazol-3-yl]sulfanyl}propyl)-7-(piperidin-1-ylsulfonyl)-1,2,3,4-tetrahydroisoquinoline $^1$H-NMR (CDCl$_3$): δ=1.4 (m, 2H); 1.7 (m, 4H); 2.1 (q, 2H); 2.5 (s, 3H); 2.6 (t, 2H); 2.7 (t, 2H); 3.0 (m, 6H); 3.3 (t, 2H); 3.5 (s, 3H); 3.6 (s, 2H); 7.2 (d, 1H); 7.45 (s, 1H); 7.5 (d, 1H); 8.9 (s, 1H).
$C_{24}H_{32}N_6O_2S_3$ (532.8).

EXAMPLE 21

2-{3-[(4-Methyl-5-phenyl-4H-1,2,4-triazol-3-yl)sulfanyl]propyl}-7-(phenylsulfonyl)-1,2,3,4-tetrahydroisoquinoline $^1$H-NMR (CDCl$_3$): δ=2.1 (q, 2H); 2.6 (t, 2H); 2.7 (t, 2H); 2.9 (t, 2H); 3.35 (t, 2H); 3.5 (s, 3H); 3.6 (m, 2H); 7.2 (d, 1H); 7.4–7.7 (m, 10H); 7.9 (d, 2H). $C_{27}H_{28}N_4O_2S_2$ (504.7).

EXAMPLE 22

2-(3-{(4-Methyl-5-(4-methyl-1,3-thiazol-5-yl)-4H-1,2,4-triazol-3-yl]sulfanyl}propyl)-1,2,3,4-tetrahydroisoquinolin-7-yl Phenylsulfone $^1$H-NMR (CDCl$_3$): δ=2.1 (q, 2H); 2.5 (s, 3H); 2.7 (t, 2H); 2.8 (t, 2H); 2.95 (t, 2H); 3.4 (t, 2H); 3.5 (s, 3H); 3.65 (m, 2H); 7.2 (d, 1H); 7.4–7.7 (m, 5H); 7.9 (d, 2H); 8.9 (s, 1H). $C_{25}H_{29}N_5O_2S_3$ (525.7).

EXAMPLE 23

2-{3-[(4-Methyl-5-phenyl-4H-1,2,4-triazol-3-yl)sulfanyl]propyl}-7-(morpholin-4-ylsulfonyl)-1,2,3,4-tetrahydroisoquinoline $^1$H-NMR (CDCl$_3$): δ=2.1 (q, 2H); 2.7 (t, 2H); 2.8 (t, 2H); 3.0 (t, 4H); 3.35 (t, 2H); 3.6 (s, 3H); 3.7 (m, 6H); 7.3 (m, 1H); 7.4–7.6 (m, 5H); 7.9 (d, 2H). $C_{25}H_{31}N_5O_3S_2$ (525.7).

EXAMPLE 24

2-[4-(4-Methyl-5-phenyl-4H-1,2,4-triazol-3-yl)butyl]-7-(phenylsulfonyl)-1,2,3,4-tetrahydroisoquinoline $C_{28}H_{30}N_4O_2S$ (486.6).

EXAMPLE 25

2-{3-[(4-Methyl-5-pyridin-3-yl-4H-1,2,4-triazol-3-yl)sulfanyl]-propyl}-N-phenyl-1,2,3,4-tetrahydroisoquinoline-7-sulfonamide $^1$H-NMR (CDCl$_3$): δ=1.3 (m, NH); 2.1 (q, 2H); 2.6 (m, 4H); 2.8 (t, 2H); 3.3 (t, 2H); 3.6 (s, 3H); 3.7 (m, 6H); 7.3 (m, 1H); 7.4–7.6 (m, 5H); 7.9 (d, 2H). $C_{26}H_{28}N_6O_2S_2$ (520.7). Melting point: 58–61° C.

EXAMPLE 26

2-(3-{[4-Methyl-5-(4-methyl-1,3-thiazol-5-yl)-4H-1,2,4-triazol-3-yl]sulfanyl}propyl)-N-phenyl-1,2,3,4-tetrahydroisoquinoline-7-sulfonamide $^1$H-NMR (CDCl$_3$): δ=2.1 (q, 2H); 2.5 (s, 3H); 2.7 (m, 4H); 2.9 (m, 2H); 3.3 (t, 2H); 3.5 (s, 3H); 3.6 (s, 32H); 7.0–7.2 (m, 6H); 7.5 (m, 2H); 8.9 (s, 1H). $C_{25}H_{28}N_6O_2S_3$ (540.7); Melting point: 77–81° C.

EXAMPLE 27

2-(3-{[5-(2,4-Dimethoxy)phenyl)-4-methyl-4H-1,2,4-triazol-3-yl]-sulfanyl}propyl)-7-(methylsulfonyl)-1,2,3,4-tetrahydroisoquinoline $^1$H-NMR (CDCl$_3$): δ=2.2 (q, 2H); 2.9 (m, 2H); 3.0 (m, 2H); 3.05 (s, 3H); 3.1 (m, 2H); 3.3 (m, 5H); 3.7 (s, 3H); 3.85 (s, 3H); 3.9 (s, 2H); 6.5 (s, 1H); 6.65 (d, 1H); 7.25 (d, 1H); 7.3 (d, 1H); 7.7 (s, 1H); 7.8 (d, 1H). $C_{24}H_{30}N_4O_4S_2$ (502.7) MS: 503.5 [M+H]$^+$.

EXAMPLE 28

6,7-Dichloro-2-{3-[(4-methyl-5-phenyl-4H-1,2,4-triazol-3-yl)-sulfanyl]propyl}-1,2,3,4-tetrahydroisoquinoline $C_{21}H_{22}Cl_2N_4S$ (433.4); Melting point: 138–139° C.

EXAMPLE 29

7,8-Dichloro-2-{3-[(4-methyl-5-phenyl-4H-1,2,4-triazol-3-yl)-sulfanyl]propyl}-1,2,3,4-tetrahydroisoquinoline Hydrochloride 1H-NMR (CDCl$_3$): δ=2.1 (q, 2H); 2.7 (m, 4H); 2.9 (t, 2H); 3.3 (t, 2H); 3.6 (s, 3H); 3.7 (s, 2H); 6.95 (d, 1H); 7.2 (d, 1H); 7.5 (m, 3H); 7.7 (m, 2H), [free base].

Salt precipitation with ethereal HCl led to the title compound $C_{21}H_{22}Cl_2N_4S$.xHCl (469.9); Melting point: 109° C.

EXAMPLE 30

7-Cyano-2-[4-(4-methyl-5-phenyl-4H-1,2,4-triazol-3-yl)butyl]-1,2,3,4-tetrahydroisoquinoline Hydrochloride $C_{23}H_{25}N_5$.HCl (407.9); Melting point: 175° C.

EXAMPLE 31

2-{3-[(4-Methyl-5-thien-3-yl-4H-1,2,4-triazol-3-yl)sulfanyl]-propyl}-6-(trifluoromethyl)-1,2,3,4-tetrahydroisoquinoline Hydrochloride $C_{20}H_{21}F_3N_4S_2$.ClxHCl (475); Melting point: 184–185° C.

EXAMPLE 32

1-{2-[3-({4-Methyl-5-[4-(trifluoromethyl)phenyl]-4H-1,2,4-triazol-3-yl}sulfanyl)propyl]-1,2,3,4-tetrahydroisoquinolin-7-yl}ethanone $^1$H-NMR (CDCl$_3$): δ=2.15 (q, 2H); 2.4 (s, 3H); 2.7 (t, 2H); 2.8 (t, 2H); 3.0 (t, 2H); 3.3 (t, 2H); 3.6 (s, 3H); 3.75 (s, 2H); 7.1 (d, 1H); 7.6–7.8 (m, 6H). $C_{24}H_{25}F_3N_4OS$ (474.5).

The hydrochloride of the title compound was obtained by treatment with ethereal hydrochloric acid: Melting point: 183° C.

EXAMPLE 33

6,7-Dichloro-2-(3-{[4-methyl-5-(4-methylphenyl)-4H-1,2,4-triazol-3-yl]sulfanyl}propyl)-1,2,3,4-tetrahydroisoquinoline Hydrochloride 1H-NMR (CDCl$_3$): δ=2.1 (q, 2H); 2.4 (s, 3H); 2.7 (m, 4H); 2.8 (t, 2H); 3.3 (t, 2H); 3.5 (s, 2H); 3.6 (s, 3H); 7.1 (s, 1H); 7.2 (s, 1H); 7.3 (d, 2H); 7.5 (d, 2H); [free base].

The title compound was obtained by treatment with ethereal hydrochloric acid $C_{22}H_{24}Cl_2N_4S \cdot HCl$ (483.9) Melting point: 207–210° C.

EXAMPLE 34

6-Chloro-2-{3-[(4-methyl-5-phenyl-4H-1,2,4-triazol-3-yl)-sulfanyl]propyl}-1,2,3,4-tetrahydroisoquinoline Hydrochloride $^1$H-NMR (CDCl$_3$): δ=2.1 (q, 2H); 2.4 (s, 3H); 2.7 (m, 4H); 2.8 (t, 2H); 3.3 (t, 2H); 3.5 (s, 2H); 3.6 (m, 5H); 6.9 (d, 1H); 7.1 (m, 2H); 7.5 (d, 3H); 7.5 (d, 2H); [free base].

Salt precipitation with ethereal HCl led to the title compound $C_{21}H_{23}ClN_4S \cdot HCl$ (435.4); Melting point: 188–191° C.

EXAMPLE 35

2-(3-{[4-Methyl-5-(1-methyl-1H-pyrrol-2-yl)-4H-1,2,4-triazol-3-yl]sulfanyl}propyl)-7-(piperidin-1-ylsulfonyl)-1,2,3,4-tetrahydroisoquinoline $^1$H-NMR (CDCl$_3$): δ=1.4 (m, 2H); 1.7 (m, 4H); 2.1 (q, 2H); 2.7 (t, 2H); 2.8 (t, 2H); 3.0 (m, 6H); 3.35 (t, 2H); 3.6 (s, 3H); 3.7 (s, 2H); 3.9 (s, 3H); 6.2 (m, 1H); 6.4 (m, 1H); 6.8 (m, 1H); 7.2 (d, 1H); 7.4 (s, 1H); 7.5 (m, 2H). $C_{25}H_{34}N_6O_2S_2$ (514.7); Melting point: 96–100° C.

EXAMPLE 36

2-[4-(4-Methyl-5-phenyl-4H-1,2,4-triazol-3-yl)butyl]-7-(piperidin-1-ylsulfonyl)-1,2,3,4-tetrahydroisoquinoline $C_{27}H_{35}N_5O_2S$ (493.7) MS: 494.3 [M+H]$^+$.

EXAMPLE 37

2-(3-{[4-Methyl-5-thien-3-yl)-4H-1,2,4-triazol-3-yl]sulfanyl}-propyl)-7-(piperidin-1-ylsulfonyl)-1,2,3,4-tetrahydroisoquinoline $^1$H-NMR (CDCl$_3$): δ=1.4 (m, 2H); 1.7 (m, 4H); 2.15 (q, 2H); 2.7 (t, 2H); 2.8 (t, 2H); 3.0 (m, 6H); 3.3 (t, 2H); 3.7 (m, 5H); 7.2 (d, 1H); 7.4 (s, 1H); 7.5 (m, 3H); 7.7 (s, 1H). $C_{24}H_{31}N_5O_2S_3$ (517.7) MS: 518.3 [M+H]$^+$; Melting point: 192–195° C.

EXAMPLE 38

2-{3-[(4-Methyl-5-phenyl-4H-1,2,4-triazol-3-yl)sulfanyl]propyl}-N-phenyl-1,2,3,4-tetrahydroisoquinoline-7-sulfonamide $^1$H-NMR (CDCl$_3$): δ=2.1 (q, 2H); 2.6 (t, 2H); 2.7 (t, 2H); 2.9 (t, 2H); 3.3 (t, 2H); 3.55 (s, 2H); 3.6 (s, 3H); 7.0 (m, 2H); 7.2 (m, 4H); 7.5 (m, 5H); 7.7 (m, 2H). $C_{27}H_{29}N_5O_2S_2$ (519.7) MS: 520.3 [M+H]$^+$.

EXAMPLE 39

6-Chloro-2-{3-[(4-methyl-5-thien-3-yl-4H-1,2,4-triazol-3-yl)-sulfanyl]propyl}-1,2,3,4-tetrahydroisoquinoline $C_{19}H_{21}ClN_4S_2$ (405); Melting point: 99–100° C.

EXAMPLE 40

7-[(Diethylammonio)methyl]-2-{3-[(4-methyl-5-phenyl-4H-1,2,4-triazol-3-yl)sulfanyl]propyl}-1,2,3,4-tetrahydroisoquinoline Dihydrochloride $C_{26}H_{35}N_5S \cdot 2HCl$ (522.6); Melting point: 75° C.

EXAMPLE 41

2-{3-[(4-Methyl-5-thien-3-yl-4H-1,2,4-triazol-3-yl) sulfanyl]-propyl}-7-(trifluoromethyl)-1,2,3,4-tetrahydroisoquinoline Hydrochloride Preparation of the Starting Material
41A 7-Trifluoromethyl-1,2,3,4-tetrahydroisoquinoline 10.0 ml of concentrated sulfuric acid were slowly added dropwise to a solution of 1.77 g (6.2 mmol) of N-trifluoroacetyl-2-(4-trifluoromethylphenyl)ethylamine [prepared from 2-(4-trifluoromethylphenyl)ethylamine and trifluoroacetic anhydride at −5° C.] in 7.5 ml of glacial acetic acid, and, while cooling in ice, 2 ml of formalin solution were added dropwise. After 18 hours at room temperature, the reaction mixture was poured into 130 ml of ice-water and extracted with dichloromethane, and the combined organic phases were washed with sodium bicarbonate solution and then with water. After drying over sodium sulfate, filtration and evaporation, 1.7 g of 2-trifluoroacetyl-7-trifluoromethyl-1,2,3,4-tetrahydroisoquinoline were isolated and were converted into 7-trifluoromethyl-1,2,3,4-tetrahydroisoquinoline by heating under reflux in ethanol/3N HCl (1:1) and alkaline workup.

Yield: 1.0 g (4.7 mmol) 75% of theory. $^1$H-NMR (CDCl$_3$): δ=2.0 (sbr, 1H); 2.9 (t, 2H); 3.2 (t, 2H); 4.0 (s, 2H); 7.2 (d, 1H); 7.3 (s, 1H); 7.4 (s, 1H).

41B 2-(3-Chloropropyl)-7-trifluoromethyl-1,2,3,4-tetrahydroisoquinoline 0.95 g (4.7 mmol) of the compound described above was reacted with 1-bromo-3-chloropropane in the same way as described in Example 4B at room temperature, and purified by chromatography (silica gel, mobile phase dichloromethane with 2% methanol).

Yield: 0.9 g (3.2 mmol) 69% of theory. $^1$H-NMR (CDCl$_3$): δ=2.0 (m, 2H); 2.65 (m, 2H); 2.75 (m, 2H); 2.9 (m, 2H); 3.65 (m, 4H); 7.2 (dd, 1H); 7.3 (d, 1H); 7.4 (dd, 1H).

41C Preparation of the Final Product 0.45 g (1.6 mmol) of 2-(3-chloropropyl)-7-trifluoromethyl-1,2,3,4-tetrahydroisoquinoline, 0.36 g (1.6 mmol) of 3-mercapto-4-methyl-5-thien-3-yl-4H-1,2,4-triazole and 40 mg of lithium hydroxide were stirred in 6 ml of DMF at 100° C. for 4 hours. Workup entailed pouring into ice/water, extraction with methyl tert-butyl ether, drying over sodium sulfate and purification after filtration and evaporation by column chromatography (silica gel, mobile phase dichloromethane with 3–5% methanol).

Yield: 0.3 g (0.7 mmol) 42% of theory. $^1$H-NMR (CDCl$_3$): δ=2.1 (m, 2H); 2.7 (t, 2H); 2.8 (t, 2H); 3.0 (m, 2H); 3.35 (t, 2H); 3.7 (m, 5H); 7.1 (d, 1H); 7.2 (s, 1H); 7.3 (d, 1H); 7.5 (m, 2H); 7.7 (s, 1H); [free base].

The title compound was obtained by treatment with ethereal HCl $C_{20}H_{21}F_3N_4S_2 \cdot HCl$ (475); Melting point: 192–194° C.

EXAMPLE 42

2-{3-[(4-Methyl-5-phenyl-4H-1,2,4-triazol-3-yl) sulfanyl]propyl}-8-(trifluoromethyl)-1,2,3,4-tetrahydroisoquinoline Hydrochloride Preparation of the Starting Materials
42A 6/8-Trifluoromethyl-1,2,3,4-tetrahydroisoquinoline 5.3 g (18.6 mmol) of N-trifluoroacetyl-2-(3-trifluoromethyl-phenyl)ethylamine [prepared from 2-(3-trifluoromethylphenyl)ethylamine and trifluoroacetic anhydride at −5° C.] and 0.9 g (29 mmol) of paraformaldehyde were added to a mixture of 22 ml of glacial acetic acid and 30 ml of concentrated sulfuric acid. After 18 hours at room temperature, the reaction mixture was poured into 350 ml of ice-water and extracted with ethyl acetate, and the combined organic phases were washed with sodium bicarbonate solution and then with water. After drying over sodium sulfate, filtration and evaporation, 5.4 g of a mixture of 2-trifluoroacetyl-6- and -8-trifluoromethyl-1,2,3,4-tetrahydroisoquinoline were isolated. The protective group was eliminated by heating in ethanol/3N HCl (1:1) under reflux. The two isomers were separated after workup and purification by chromatography (silica gel, mobile phase dichloromethane with 2–4% methanol):

F1 1.2 g (5.7 mmol) 32% of theory of 8-trifluoromethyl-1,2,3,4-tetrahydroisoquinoline $^1$H-NMR (CDCl$_3$): δ=1.9 (sbr, 1H); 2.8 (t, 2H); 3.1 (t, 2H); 4.2 (s, 2H); 7.2 (m, 2H); 7.5 (d, 1H).

F2 1.4 g (6.8 mmol) 38% of theory of 6-trifluoromethyl-1,2,3,4-tetrahydroisoquinoline $^1$H-NMR (CDCl$_3$): δ=1.8 sbr, 1H); 2.8 (t, 2H); 3.1 (t, 2H); 4.0 (s, 2H); 7.1 (d, 1H); 7.4 (m, 2H).

42 B 2-(3-Chloropropyl)-8-trifluoromethyl-1,2,3,4-tetrahydroisoquinoline 2-(3-Chloropropyl)-8-trifluoromethyl-1,2,3,4-tetrahydroisoquinoline was obtained in 73% yield by reacting 42-A F1 with bromochloropropane in a manner analogous to the description in Example 4C.

$^1$H-NMR (CDCl$_3$): δ=2.0 (q, 2H); 2.7–2.8 (m, 4H); 3.0 (t, 2H); 3.6 (t, 2H); 3.8 (s, 2H); 7.2–7.3 (m, 2H); 7.4 (d, 1H).

42C Preparation of the Final Compound

Reaction of 0.7 g (3.0 mmol) of 3-mercapto-4-methyl-5-phenyl-1,2,4(4H)-triazole with 0.83 g (3.0 mmol) of 2-(3-chloropropyl)-8-trifluoromethyl-1,2,3,4-tetrahydroisoquinoline [42B1] in 10 ml of DMF in the presence of 70 mg of lithium hydroxide at 100° C. afforded, after workup as described under 4D, 0.84 g (1.9 mmol) of the final compound.

Yield: 0.84 g (1.9 mmol) 65% of theory $^1$H-NMR (CDCl$_3$): δ=2.1 (q, 2H); 2.6–2.7 (m, 4H); 2.9 (t, 2H); 3.4 (t, 2H); 3.6 (s, 3H); 3.8 (s, 2H); 7.1 (t, 1H); 7.25 (d, 1H); 7.4 (d, 1H), 7.5 (m, 3H); 7.6 (m, 2H).

The title compound was obtained by treatment with ethereal HCl. $C_{22}H_{23}F_3N_4S.HCl$ (469); Melting point: 118° C.

EXAMPLE 43

2-{3-[(4-Methyl-5-phenyl-4H-1,2,4-triazol-3-yl)sulfanyl]propyl}-6-(trifluoromethyl)-1,2,3,4-tetrahydroisoquinoline Hydrochloride Preparation of the Starting Materials 43 B2 2-(3-Chloropropyl)-6-trifluoromethyl-1,2,3,4-tetrahydroisoquinoline 2-(3-Chloropropyl)-6-trifluoromethyl-1,2,3,4-tetrahydroisoquinoline was obtained in 96% yield by reacting 6-trifluoromethyl-1,2,3,4-tetrahydroisoquinoline [42AF2] (obtained as described in 42A) with bromochloropropane in a manner analogous to that described for 4C.

$^1$H-NMR (CDCl$_3$): δ=2.0 (m, 2H); 2.6–2.8 (m, 4H); 2.9 (t, 2H); 3.6 (m, 4H); 7.1 (d, 1H); 7.4 (m, 2H).

43C Preparation of the Final Compound

Reaction of 0.7 g (3.0 mmol) of 3-mercapto-4-methyl-5-phenyl-1,2,4(4H)-triazole with 0.83 g (3.0 mmol) of 2-(3-chloropropyl)-6-trifluoromethyl-1,2,3,4-tetrahydroisoquinoline in 10 ml of DMF in the presence of 70 mg of lithium hydroxide at 100° C. afforded, after workup as described under 4D, 0.75 g (1.7 mmol) of the final compound.

Yield: 0.75 g (1.7 mmol) 58% of theory; $^1$H-NMR (CDCl$_3$): δ=2.1 (q, 2H); 2.6 (t, 2H); 2.7 (t, 2H); 2.9 (t, 2H); 3.3 (t, 2H); 3.6 (s, 3H); 3.7 (s, 2H); 7.1 (d, 1H); 7.3 (m, 2H); 7.5 (m, 3H); 7.7 (m, 2H); [free base].

The title compound was obtained by treatment with ethereal HCl $C_{22}H_{23}F_3N_4S.HCl$ (469); Melting point: 200–202° C.

EXAMPLE 44

2-{3-[(4-Methyl-5-phenyl-4H-1,2,4-triazol-3-yl)sulfanyl]propyl}-7-(trifluoromethyl)-1,2,3,4-tetrahydroisoquinoline Hydrochloride $C_{22}H_{23}F_3N_4S.HCl$ (469); Melting point: 205–207° C.

EXAMPLE 45

2-{3-[(4-Methyl-5-(thien-3-yl)-4H-1,2,4-triazol-3-yl)sulfanyl]-propyl}-7-(4-methylpiperazin-1-ylsulfonyl)-1,2,3,4-tetrahydroisoquinoline $^1$H-NMR (CDCl$_3$): δ=2.1 (q, 2H); 2.2 (s, 3H); 2.4 (m, 4H); 2.7 (t, 2H); 2.8 (t, 2H); 2.9 (t, 2H); 3.0 (m, 4H); 3.3 (t, 2H); 3.6 (m, 5H); 7.2 (d, 2H); 7.45 (m, 4H); 7.7 (m, 1H). $C_{24}H_{32}N_6O_2S_3$ (538.8).

EXAMPLE 46

2-{3-[(4-Methyl-5-(phenyl)-4H-1,2,4-triazol-3-yl)sulfanyl]-propyl}-7-(4-methylpiperazin-1-ylsulfonyl)-1,2,3,4-tetrahydroisoquinoline $^1$H-NMR (CDCl$_3$): δ=2.1 (q, 2H); 2.2 (s, 3H); 2.5 (m, 4H); 2.7 (t, 2H); 2.8 (t, 2H); 2.9–3.0 (m, 6H); 3.3 (t, 2H); 3.6 (s, 3H); 3.7 (s, 2H); 7.2 (d, 1H); 7.5 (m, 5H); 7.6 (m, 2H). $C_{26}H_{34}N_6O_2S_3$ (564.8).

EXAMPLE 47

2-{3-[(4-Methyl-5-(thien-3-yl)-4H-1,2,4-triazol-3-yl)sulfanyl]-propyl}-7-(1,2,3,4-tetrahydroisoquinolin-1-ylsulfonyl)-1,2,3,4-tetrahydroisoquinoline $^1$H-NMR (CDCl$_3$): δ=2.1 (q, 2H); 2.7 (t, 2H); 2.8 (t, 2H); 2.9 (t, 2H); 3.2–3.3 (m, 4H); 3.6 (m, 2H); 3.7 (m, 5H); 4.2 (m, 2H); 7.1 (m, 4H); 7.2 (d, 1H); 7.4–7.6 (m, 4H); 7.7 (m, 1H). $C_{28}H_{31}N_5O_2S_3$ (565).

EXAMPLE 48

2-{3-[(4-Methyl-5-(pyrid-3-yl)-4H-1,2,4-triazol-3-yl)sulfanyl]-propyl}-7-(1,2,3,4-tetrahydroisoquinolin-1-ylsulfonyl)-1,2,3,4-tetrahydroisoquinoline $^1$H-NMR (CDCl$_3$) δ=2.1 (q, 2H); 2.7 (t, 2H); 2.8 (t, 2H); 2.9 (m, 4H); 3.3 (m, 4H); 3.6 (s, 3H); 3.7 (s, 2H); 4.2 (s, 2H); 7.0–7.2 (m, 5H); 7.2 (m, 1H); 7.4–7.6 (m, 3H); 8.0 (m, 1H); 8.7 (m, 1H); 8.9 (m, 1H). $C_{29}H_{32}N_6O_2S_2$ (558).

EXAMPLE 49

7-[(3,3-Dimethylpiperidin-1-yl)sulfonyl]-2-{3-[(4-methyl-5-phenyl-4H-1,2,4-triazol-3-yl)sulfanyl]propyl}-1,2,3,4-tetrahydroisoquinoline $C_{28}H_{37}N_5O_2S_2$ (539.8); Melting point: 75–76° C.

EXAMPLE 50

2-{3-[(4-Cyclopropyl-5-phenyl-4H-1,2,4-triazol-3-yl)sulfanyl]-propyl}-7-[(3,3-dimethylpiperidin-1-yl)sulfonyl]-1,2,3,4-tetrahydroisoquinoline $C_{30}H_{39}N_5O_2S_2$ (558).

EXAMPLE 51

2-[(4-{[(4-Methyl-5-(1-methyl-1H-pyrrol-3-yl)-4H-1,2,4-triazol-3-yl)sulfanyl]methyl}cyclohexyl)methyl]-7-nitro-1,2,3,4-tetrahydroisoquinoline $C_{26}H_{31}N_5O_2S$ (477.6); Melting point: 160° C.

EXAMPLE 52

2-{(E)-4-[(4-Methyl-5-pyridin-3-yl-4H-1,2,4-triazol-3-yl)-sulfanyl]but-2-enyl}-7-nitro-1,2,3,4-tetrahydroisoquinoline $C_{21}H_{22}N_6O_2S$ (422) MS: 423 [M+H]$^+$.

EXAMPLE 53

2-[(4-{[(4-Methyl-5-pyridin-3-yl-4H-1,2,4-triazol-3-yl)sulfanyl]-methyl}cyclohexyl)methyl]-1,2,3,4-tetrahydroisoquinolin-7-carbonitrile $C_{27}H_{31}N_5S$ (457.6); Melting point: 156–158° C.

EXAMPLE 54

1-(2-{3-[(4-Methyl-5-(3-cyano)phenyl-4H-1,2,4-triazol-3-yl)sulfanyl]propyl}-1,2,3,4-tetrahydroisoquinolin-7-yl)ethanone Hydrochloride $C_{24}H_{25}N_5OS \times HCl$ (468); Melting point: 185° C.

EXAMPLE 55

7-Nitro-2-[(4-{[(4-methyl-5-pyridin-3-yl-4H-1,2,4-triazol-3-yl)-sulfanyl]-methyl}cyclo-hexyl)methyl]-1,2,3,4-tetrahydroisoquinoline $C_{26}H_{31}N_6O_2S$ (477.6); Melting point: 160° C.

EXAMPLE 56

1-{2-[3-({4-Methyl-5-phenyl]-4H-1,2,4-triazol-3-yl}sulfanyl)-propyl]-1,2,3,4-tetrahydroisoquinolin-7-yl}ethanone Hydrochloride $C_{23}H_{27}N_4OS \times HCl$ (443); Melting point: 165° C.

EXAMPLE 57

7,8-Dichloro-2-{3-[(4-methyl-5-phenyl-4H-1,2,4-triazol-3-yl)-sulfanyl]propyl}-1,2,3,4-tetrahydroisoquinoline $C_{21}H_{22}ClN_4S$ (399); Melting point: 72–75° C.

EXAMPLE 58

1-{2-[3-({5-(2,4-Dinitrophenyl)-4-methyl]-4H-1,2,4-triazol-3-yl}-sulfanyl)propyl]-1,2,3,4-tetrahydroisoquinolin-7-yl}ethanone Hydrochloride $C_{23}H_{25}N_6O_5S \times HCl$ (500.6); Melting point: 193° C.

EXAMPLE 59

2-{3-[(4-Methyl-5-phenyl-4H-1,2,4-triazol-3-yl)sulfanyl]propyl}-7-(octahydroisoquinolin-2(1H)-ylsulfonyl)-1,2,3,4-tetrahydroisoquinoline $C_{30}H_{39}N_5O_2S_2$ (565.8) MS: 567 [M+H]$^+$.

EXAMPLE 60

2-{3-[(4-Methyl-5-pyridin-3-yl-4H-1,2,4-triazol-3-yl)sulfanyl]-propyl}-7-(octahydroisoquinolin-2(1H)-ylsulfonyl)-1,2,3,4-tetrahydroisoquinoline $C_{29}H_{38}N_6O_2S_2$ (566.8) MS: 568 [M+H]$^+$.

EXAMPLE 61

2-{3-[(4-Cyclopropyl-5-phenyl-4H-1,2,4-triazol-3-yl)sulfanyl]-propyl}-7-(azepan-1-ylsulfonyl)-1,2,3,4-tetrahydroisoquinoline $C_{29}H_{37}N_5O_2S_2$ (551.8) MS: 552 [M]$^+$.

EXAMPLE 62

2-{3-[(4-Methyl-5-phenyl-4H-1,2,4-triazol-3-yl)sulfanyl]propyl}-7-(pyrrolidin-1-ylsulfonyl)-1,2,3,4-tetrahydroisoquinoline $C_{25}H_{31}N_5O_2S_2$ (497.7).

EXAMPLE 63

2-{3-[(4-Methyl-5-phenyl-4H-1,2,4-triazol-3-yl)sulfanyl]propyl}-7-(azepan-1-ylsulfonyl)-1,2,3,4-tetrahydroisoquinoline $C_{27}H_{35}N_5O_2S_2$ (525.7).

EXAMPLE 64

7-Chlor-2-(3-{[4-methyl-5-phenyl-4H-1,2,4-triazol-3-yl]sulfanyl}-but-2-en-yl)-1,2,3,4-tetrahydroisoquinoline $C_{21}H_{23}ClN_4S$ (399); Melting point: 72–75° C.

EXAMPLE 65

2-(3-{[4-Methyl-5-methylamino-4H-1,2,4-triazol-3-yl]sulfanyl}-propyl)-7-(azepan-1-ylsulfonyl)-1,2,3,4-tetrahydroisoquinoline

EXAMPLE 66

N,4-Dimethyl-5-{[3-(7-(piperidin-1-ylsulfonyl)-3,4-dihydroisoquinolin-2(1H)-yl)propyl]sulfanyl}-4H-1,2,4-triazol-3-amine

EXAMPLE 67

7-tert-Butyl-2-(3-{[4-methyl-5-(4-methyl-1,3-thiazol-5-yl)-4H-1,2,4-triazol-3-yl]sulfanyl}propyl)-1,2,3,4-tetrahydroisoquinoline

EXAMPLE 68

2-{3-[(4-Methyl-5-pyridin-3-yl-4H-1,2,4-triazol-3-yl)sulfanyl]-propyl}-7-(azepan-1-ylsulfonyl)-1,2,3,4-tetrahydroisoquinoline

EXAMPLE 69

7-({4-[2-tert-Butyl-6-(trifluoromethyl)pyrimidin-4-yl]piperazin-1-yl}sulfonyl)-2-{3-[(4-methyl-5-phenyl-4H-1,2,4-triazol-3-yl)-sulfanyl]propyl}-1,2,3,4-tetrahydroisoquinoline

EXAMPLE 70

8-Brom-2-(3-{[5-cyclohexyl-4-methyl-4H-1,2,4-triazol-3-yl]sulfanyl}but-2-en-yl)-1,2,3,4-tetrahydroisoquinoline

EXAMPLE 71

4-Methyl-5-phenyl-N-[4-(7-(pyrrolidin-1-ylsulfonyl)-1,2,3,4-tetrahydroisoquinolin-2-yl)butyl]-4H-1,2,4-triazole-3-carboxamide

EXAMPLE 72

6-Methyl-2-(3-{[4-methyl-5-(1-methyl-1H-pyrrol-3-yl)-4H-1,2,4-triazol-3-yl]sulfanyl}-propyl)-7-(pyrrolidin-1-ylsulfonyl)-1,2,3,4-tetrahydroisoquinoline

EXAMPLE 73

7-Cyano-2-[(2-{[(4-Methyl-5-pyridin-3-yl-4H-1,2,4-triazol-3-yl)-sulfanyl]-methyl}-cyclopropyl)methyl]-1,2,3,4-tetrahydroisoquinoline

EXAMPLE 74

1-(2-{3-[(4-Methyl-5-(3-methoxy)phenyl-4H-1,2,4-triazol-3-yl)-oxy]propyl}-1,2,3,4-tetrahydroisoquinolin-7-yl)ethanone

EXAMPLE 75

4-(7-(Pyrrolidin-1-ylsulfonyl)-1,2,3,4-tetrahydroisoquinoline-2-yl)butyl-4-methyl-5-phenyl-4H-1,2,4-triazole-3-carboxylate

EXAMPLE 76

2-[2-({[5-(N-Methyl)pyrrol-2-yl)-4-methyl-4H-1,2,4-triazol-3-yl]-sulfanyl}methyl)prop-2-enyl]-1,2,3,4-tetrahydroisoquinolin-7-carboxamide

EXAMPLE 77

2-{3-[(4-Cyclopropyl-5-(4-methylsulfonyl)phenyl-4H-1,2,4-triazol-3-yl)sulfanyl]propyl}-7-(pyrrolidin-1-ylsulfonyl)-1,2,3,4-tetrahydroisoquinoline

EXAMPLE 78

6-tert-Butyl-2-(3-{[5-(2,4-dinitrophenyl)-4-methyl-4H-1,2,4-triazol-3-yl]sulfanyl}propyl)-1,2,3,4-tetrahydroisoquinoline

EXAMPLE 79

N-[2-(8-{[5-(Dimethylamino)-4-butyl-4H-1,2,4-triazol-3-yl]sulfanyl}octyl)-1,2,3,4-tetrahydroisoquinolin-7-yl]methansulfonamide

EXAMPLE 80

2-{3-[(4-Methyl-5-pyrazin-2-yl-4H-1,2,4-triazol-3-yl)sulfanyl]-propyl}-7-(octahydroisoquinolin-2(1H)-ylsulfonyl)-1,2,3,4-tetrahydroisoquinoline

EXAMPLE 81

7-Cyano-2-{3-[(4-methyl-5-(2-methyloxazol-4-yl)-4H-1,2,4-triazol-3-yl)sulfanyl]propyl}-1,2,3,4-tetrahydroisoquinoline

EXAMPLE 82

2-{6-[(5-(2,5-Dimethylfuran-3-yl)-4-methyl-4H-1,2,4-triazol-3-yl)sulfanyl]hexyl}-7-trifluormethansulfonyloxy-1,2,3,4-tetrahydroisoquinoline

EXAMPLE 83

2-[2-({[4-methyl-5-phenyl-4H-1,2,4-triazol-3-yl]sulfanyl}methyl)-prop-2-enyl]-7-nitro-1,2,3,4-tetrahydroisoquinoline Hydrochloride $C_{22}H_{23}N_5O_2S \times HCl$ (460); Melting point: 146–150° C.

EXAMPLE 84

N-[2-(3-{[4-Methyl-5-phenyl-4H-1,2,4-triazol-3-yl]sulfanyl}-propyl)-1,2,3,4-tetrahydroisoquinolin-7-yl]methansulfonamide $C_{22}H_{27}N_5O_2S_2 \times HCl$ (494.1); Melting point: 90° C.

The following compounds can be prepared in an analogous way in principle:

TABLE 1

| Ex. | $R^1$ | $R^2$ | A | $R^6$ | $R^7$ | $R^8$ |
|---|---|---|---|---|---|---|
| 85 | Me | Ethoxycarbonyl | S—$(CH_2)_3$— | 7-(piperidin-1-yl-sulfonyl) | 8-methyl | |
| 86 | Me | N,N-Dimethylamino- | S—$CH_2$—CH=CH—$CH_2$— | 6-methyl | 7-cyano | |
| 87 | Et | tert.Butyl | $(CH_2)_4$— | 7-cyano | | |
| 88 | Butyl | Methylsulfanyl | $(CH_2)_4$— | 6-fluoro | | |
| 89 | cycProp | Methyl | S—$(CH_2)_3$— | 6-chloro | 7-chloro | |
| 90 | Me | 2,5-Di-methyl-furanyl-3- | S—$CH_2$—CH=CH—$CH_2$— | 7-(piperidin-1-yl-sulfonyl) | | |
| 91 | Me | 3-Thienyl | COO—$(CH_2)_3$— | 7-(piperidin-1-yl-sulfonyl) | | |
| 92 | Me | Phenyl- | $(CH_2)_4$— | 7-(3,3-dimethyl-piperidin-1-yl-sulfonyl) | | |

TABLE 1-continued

| Ex. | R¹ | R² | A | R⁶ | R⁷ | R⁸ |
|---|---|---|---|---|---|---|
| 93 | Me | 2,4-Dimethoxyphenyl | S—(CH$_2$)$_3$— | 7-methansulfonamid | | |
| 94 | Me | Amino- | S—CH$_2$—C(=CH$_2$)—CH$_2$ | 7-(piperidin-1-yl-sulfonyl) | | |
| 95 | Prop | Phenyl | S—CH$_2$—C(CH$_3$)=CH—CH$_2$— | 8-trifluoromethyl | | |
| 96 | Me | 2-Me-4-Oxazolyl- | S—(CH$_2$)$_3$— | 7-(dimethylamino-sulfonyl) | | |
| 97 | Me | 3-Benzthienyl- | S—(CH$_2$)$_6$— | 7-(pyrolidin-1-yl-sulfonyl) | | |
| 98 | Me | Phenyl- | S—(CH$_2$)$_7$— | 7-(pyrolidin-1-yl-sulfonyl) | | |
| 99 | Me | Phenyl | CONH—(CH$_2$)$_4$— | 7-(piperidin-1-yl-sulfonyl) | | |
| 100 | Me | 2-Pyrazinyl- | S—(CH$_2$)$_3$— | 7-trifluoromethyl | | |
| 101 | Phenyl | Methyl | (CH$_2$)$_4$— | 7-(morpholin-1-yl-sulfonyl) | | |
| 102 | Me | Tetrazolyl- | S—(CH$_2$)$_3$— | 7-methoxy | | |
| 103 | Et | 4-Methylthiazol-5-yl | S—(CH$_2$)$_3$— | 7-methylsulfonyl | | |
| 104 | Et | 3-Jod-phenyl | S—(CH$_2$)$_3$— | 7-methansulfonamid | | |
| 105 | Et | 4-Methylphenyl | S—CH$_2$—C(=CH$_2$)—CH$_2$ | 7-(piperidin-1-yl-sulfonyl) | | |
| 106 | Me | N-Methyl-2-Pyrrolyl- | S—(CH$_2$)$_3$— | 7-(dimethylamino-sulfonyl) | | |
| 107 | Me | 4-Methylthiazol-5-yl | S—CH$_2$—C(=CH$_2$)—CH$_2$ | 7-(pyrrolidin-1-yl-sulfonyl) | | |
| 108 | Me | 2,5-Di-methyl-furanyl-3- | S—(CH$_2$)$_3$— | 7-phenylsulfonyl | | |
| 109 | Me | 2-Me-4-Oxazolyl- | (CH$_2$)$_2$—CH(CH$_3$)—CH$_2$—CH$_2$— | 7-(morpholin-1-yl-sulfonyl) | | |
| 110 | Me | Phenyl- | S—(CH$_2$)$_7$— | 7-(pyrrolidin-1-yl-sulfonyl) | | |
| 111 | Hexyl | 3-Pyridyl- | S—(CH$_2$)$_3$— | 6-chloro | 7-chloro | |
| 112 | Me | 3-Cyano-phenyl | S—(CH$_2$)$_3$— | 7-(dimethylamino-sulfonyl) | | |
| 113 | Me | 2-Pyrazinyl- | CO—(CH$_2$)$_3$— | 7-(morpholin-1-yl-sulfonyl) | | |
| 114 | Prop | Phenyl | S—(CH$_2$)$_4$— | 7-(morpholin-1-yl-sulfonyl) | | |
| 115 | Me | 3-Metoxyphenyl | (CH$_2$)$_4$— | 6-triflourmethyl | | |
| 116 | Me | 3-Pyrrolyl | S—(CH$_2$)$_3$— | 7-nitro | | |
| 117 | Et | 3-Pyridyl | S—(CH$_2$)$_7$— | 6-methyl | 7-cyano | |
| 118 | Me | 4-Methylthiazol-5-yl | O—(CH$_2$)$_3$— | 7-(piperidin-1-yl-sulfonyl) | | |
| 119 | Me | Phenyl | CONH—(CH$_2$)$_4$— | 7-cyano | | |
| 120 | Et | 2,5-Di-methyl-furanyl-3- | S—(CH$_2$)$_3$— | 7-nitro | | |
| 121 | Et | N-Methyl-2-Pyrrolyl- | S—(CH$_2$)$_3$— | 7-nitro | | |
| 122 | Prop | Phenyl- | S—(CH$_2$)$_3$— | 6-methyl | 7-(azepan-1-yl-sulfonyl) | |
| 123 | Et | N-Propyl-tetrazolyl- | S—(CH$_2$)$_3$— | 7-cyano | | |
| 124 | Me | 3-Thienyl | S—(CH$_2$)$_3$— | 7-methylsulfonyl | | |
| 125 | Me | 4-Methoxyphenyl | S—(CH$_2$)$_3$— | 4-methoxy | | |
| 126 | Me | Tetrazolyl- | S—(CH$_2$)$_3$— | 7-(dimethylamino-sulfonyl) | | |
| 127 | Me | 4-Methylthiazol-5-yl | S—CH$_2$-cycHex-CH$_2$—CH$_2$— | 7-phenylsulfonyl | | |
| 128 | Me | 2-Chloro-phenyl | CO—(CH$_2$)$_3$— | 7-trifluoromethoxy | | |
| 129 | Et | Phenyl- | S—(CH$_2$)$_3$— | 6-CH$_2$—CH$_2$—CH$_2$—CH$_2$-7 | | |
| 130 | Et | 4-Methoxyphenyl | (CH$_2$)$_2$—CH(CH$_3$)—CH$_2$—CH$_2$— | 7-(piperidin-1-yl-sulfonyl) | | |
| 131 | Et | 4-Methylthiazol-5-yl | S—CH$_2$—C(=CH$_2$)—CH$_2$ | 7-(azepan-1-yl-sulfonyl) | | |
| 132 | Me | 2-Me-4-Oxazolyl- | S—(CH$_2$)$_6$— | 7-nitro | | |
| 133 | Me | 5-Methyl imidazol-4-yl- | S—(CH$_2$)$_3$— | 7-(piperidin-1-yl-sulfonyl) | | |
| 134 | Me | 3-Jod-phenyl | S—(CH$_2$)$_3$— | 7-(dimethylamino-sulfonyl) | | |

TABLE 1-continued

| Ex. | R¹ | R² | A | R⁶ | R⁷ | R⁸ |
|---|---|---|---|---|---|---|
| 135 | Me | Phenylmethyl | S—CH₂—CH=CH—CH₂— | 7-(azepan-1-yl-sulfonyl) | | |
| 136 | Et | Phenyl- | S—(CH₂)₃— | 6-CH(CH₃)CH₂—N(CH₃)-7 | | |
| 137 | Et | 3-Thienyl | S—(CH₂)₃— | 7-(dimethylamino-sulfonyl) | | |
| 138 | Me | 3-Jod-phenyl | S—(CH₂)₃— | 7-(piperidin-1-yl-sulfonyl) | | |
| 139 | Et | Phenyl | S—(CH₂)₃— | 8-trifluoromethyl | | |
| 140 | Me | Phenyl | CONH—(CH₂)₅— | 8-triflouromethyl | | |
| 141 | Me | Phenyl- | S—CH₂—CH=CH—CH₂— | 7-(piperidin-1-yl-sulfonyl) | | |
| 142 | Me | Cyclohexyl- | S—(CH₂)₃— | 7-nitro | | |
| 143 | iProp | 3-Pyridyl | S—(CH₂)₇— | 7-chloro | | 8-chloro |
| 144 | Me | Amino- | S—(CH₂)₃— | 7-cyano | | |
| 145 | Me | 2-Aminothiazol-4yl- | S—(CH₂)₃— | 7-cyano | | |
| 146 | Me | 3-Pyrrolyl | S—CH₂-cycProp-CH₂— | 6-triflourmethyl | | |
| 147 | cycProp | Phenyl- | S—(CH₂)₃— | 6-CH₂—CH₂—CH₂—CH₂-7 | | |
| 148 | Me | 2-Pyrazinyl- | S—(CH₂)₃— | 7-(piperidin-1-yl-sulfonyl) | | |
| 149 | Me | Cyclohexyl- | S—(CH₂)₃— | 7-cyano | | |
| 150 | Me | 5-Methyl imidazol-4-yl- | (CH₂)₂—CH(CH₃)—CH₂—CH₂— | tert-Butyl | | |
| 151 | Me | Methylamino- | S—(CH₂)₃— | 7-cyano | | |
| 152 | Me | 3-Benzthienyl- | S—(CH₂)₃— | 7-(dimethylamino-sulfonyl) | | |
| 153 | Me | Phenyl | S—CH₂-cycHex-CH₂—CH₂— | 5-methoxy | | |
| 154 | Me | Pyridin-4-yl- | S—(CH₂)₃— | 7-(piperidin-1-yl-sulfonyl) | | |
| 155 | Prop | Phenyl- | S—CH₂—C(=CH₂)—CH₂ | 7-(azepan-1-yl-sulfonyl) | | |
| 156 | Me | 3-Pyridinyl | S—(CH₂)₈— | 7-CHF₂ | | |
| 157 | Me | Tetrazolyl- | (CH₂)₄— | 7-(pyrolidin-1-yl-sulfonyl) | | |
| 158 | Me | 4-Phenyl | S—CH₂-cyc-Prop-(CH₂)₂— | 7-bromo | | |
| 159 | Me | 4-Methylphenyl | COO—(CH₂)₄— | 7-nitro | | |
| 160 | Et | 3-Cyano-phenyl | S—CH₂-cycHex-CH₂—CH₂— | 6-Methyl | | |
| 161 | Et | 2-Aminothiazol-4yl- | S—(CH₂)₃— | 7-(piperidin-1-yl-sulfonyl) | | |
| 162 | Et | Phenyl- | (CH₂)₄— | 7-(3,3-dimethyl-piperidin-1-yl-sulfonyl) | | |
| 163 | Me | 4-Methylthiazol-5-yl | S—(CH₂)₃— | 7-trifluoromethyl | | |
| 164 | Me | Oxadiazol-2-yl | S—(CH₂)₃— | 7-(dimethylamino-sulfonyl) | | |
| 165 | Me | 6-Chloro-biphenyl-2- | S—(CH₂)₃— | 7-methylsulfonyl | | |
| 166 | Et | 3-Pyridinyl | S—(CH₂)₈— | 7-CHF₂ | | |
| 167 | Me | Pyridin-3-yl- | S—(CH₂)₃— | 7-methylsulfonyl | | |
| 168 | Me | Phenyl | CONH—(CH₂)₄— | 7-Phenylsulfonyl | | |
| 169 | Et | 2-Me-4-Oxazolyl- | S—(CH₂)₃— | 8-trifluoromethyl | | |
| 170 | Me | 5-Methyl imidazol-4-yl- | S—(CH₂)₃— | 7-nitro | | |
| 171 | iProp | Phenyl | S—(CH₂)₃— | 6-bromo | | |
| 172 | Prop | 4-Imidazolyl- | S—(CH₂)₃— | 7-methoxy | | |
| 173 | Me | Tetrazolyl- | S—(CH₂)₃— | 7-cyano | | |
| 174 | Et | Phenyl | CONH—(CH₂)₄— | 6-chloro | 7-chloro | |
| 175 | Me | 2-Pyrazinyl- | S—(CH₂)₃— | 7-methoxy | | |
| 176 | Prop | Phenyl- | S—(CH₂)₃— | 6-methyl | 7-nitro | |
| 177 | Me | 4-Jod-phenyl | COO—(CH₂)₄— | 7-cyano | | |
| 178 | iProp | 4-Imidazolyl- | S—CH₂—CH=CH—CH₂— | 7-(azepan-1-yl-sulfonyl) | | |
| 179 | Et | 4-Methylsulfonyl-phenyl | S—(CH₂)₈— | 7-(piperidin-1-yl-sulfonyl) | | |
| 180 | Butyl | N-Propyl-tetrazolyl- | S—(CH₂)₃— | 7-cyano | | |
| 181 | Me | 2-Me-4-Oxazolyl- | S—CH₂—C(CH₃)=CH—CH₂— | 7-(azepan-1-yl-sulfonyl) | | |
| 182 | Et | 3-Pyrrolyl | S—(CH₂)₃— | 7-nitro | | |
| 183 | Me | N-Propyl-tetrazolyl- | S—CH₂—C(=CH₂)—CH₂ | 7-(piperidin-1-yl-sulfonyl) | | |

TABLE 1-continued

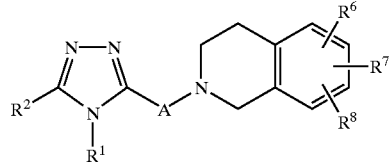

| Ex. | R¹ | R² | A | R⁶ | R⁷ | R⁸ |
|---|---|---|---|---|---|---|
| 184 | Me | Propyl | CO—(CH₂)₃— | 5-methoxy | | |
| 185 | Me | 2-Pyrazinyl- | O—(CH₂)₃— | 7-(piperidin-1-yl-sulfonyl) | | |
| 186 | Me | Oxadiazol-2-yl | S—(CH₂)₃— | 7-nitro | | |
| 187 | Prop | 2-Me-4-Oxazolyl- | S—(CH₂)₃— | 7-(piperidin-1-yl-sulfonyl) | | |
| 188 | Hexyl | Phenyl | (CH₂)₄— | 8-nitro | | |
| 189 | Prop | Phenyl | O—(CH₂)₃— | 7-methoxy | | |
| 190 | Me | 3-Pyridyl | S—(CH₂)₇— | 7-chloro | | 8-chloro |
| 191 | Et | Oxadiazol-2-yl | S—(CH₂)₃— | 7-nitro | | |
| 192 | Et | Phenyl- | S—(CH₂)₃— | 6-CH(CH₃)CH₂—NH-7 | | |
| 193 | Me | 3-Jod-phenyl | S—(CH₂)₃— | 7-methansulfonamid | | |
| 194 | Me | Pyridin-4-yl- | S—(CH₂)₃— | 7-nitro | | |
| 195 | Me | 4-Imidazolyl- | S—(CH₂)₃— | 7-(dimethylamino-sulfonyl) | | |
| 196 | Me | Phenyl | (CH₂)₄— | 8-nitro | | |
| 197 | Me | 4-Methylphenyl | S—(CH₂)₃— | 7-(piperidin-1-yl-sulfonyl) | | |
| 198 | cycProp | Phenyl | S—(CH₂)₃— | 7-Carboxamid | | |
| 199 | Me | 3-Jod-phenyl | O—(CH₂)₃— | 7-(piperidin-1-yl-sulfonyl) | | |
| 200 | Me | Cyclohexyl- | S—(CH₂)₆— | 7-(piperidin-1-yl-sulfonyl) | | |
| 201 | Me | 3-Jod-phenyl | S—CH₂—C(CH₃)=CH—CH₂— | 7-(piperidin-1-yl-sulfonyl) | | |
| 202 | Me | 3-Jod-phenyl | S—(CH2)₃— | 7-phenylsulfonyl | | |
| 203 | Butyl | Pyridin-3-yl- | O—(CH₂)₃— | 7-(piperidin-1-yl-sulfonyl) | | |
| 204 | cycProp | 2,4-Dimethoxyphenyl | S—(CH₂)₃— | 7-methansulfonamid | | |
| 205 | Me | N-Propyl-tetrazolyl- | S—(CH₂)₃— | 7-cyano | | |
| 206 | Et | 4-Methoxyphenyl | S—CH₂—CH=CH—CH₂— | 7-(piperidin-1-yl-sulfonyl) | | |
| 207 | Et | Phenyl- | S—(CH₂)₃— | 6-methyl | 7-nitro | |
| 208 | Et | Phenyl- | (CH₂)₂—CH(CH₃)—CH₂—CH₂— | 6-methoxy | | |
| 209 | Me | 3-Br-Pyridin-5-yl- | S—(CH₂)₃— | 7-nitro | | |
| 210 | Me | Methylamino- | S—CH₂-cycHex-CH₂—CH₂— | 7-cyano | | |
| 211 | Et | tert.-Butyl | CO—(CH₂)₃— | 6-methoxy | | |
| 212 | Me | Phenyl | S—(CH₂)₃— | 6-Fluoro | | |
| 213 | Me | Phenylmethyl | S—(CH₂)₃— | 7-(piperidin-1-yl-sulfonyl) | | |
| 214 | iProp | 4-Methoxyphenyl | S—CH₂—CH=CH—CH₂— | 7-(piperidin-1-yl-sulfonyl) | | |
| 215 | iProp | 4-Cyano-phenyl | S—CH₂—C(CH₃)=CH—CH₂— | 7-(piperidin-1-yl-sulfonyl) | | |
| 216 | Me | 3-Br-Pyridin-5-yl- | S—(CH₂)₃— | 7-(dimethylamino-sulfonyl) | | |
| 217 | Me | Phenyl- | S—(CH₂)₃— | 6-CH₂—CH₂—CH₂—CH₂-7 | | |
| 218 | Me | 3-Cyano-phenyl | S—(CH₂)₃— | 7-(piperidin-1-yl-sulfonyl) | | |
| 219 | Me | 3-Thienyl | S—(CH₂)₃— | 7-(dimethylamino-sulfonyl) | | |
| 220 | Et | Phenyl | (CH₂)₄— | 8-nitro | | |
| 221 | Me | Amino | S—(CH₂)₃— | 7-nitro | | |
| 222 | Me | 4-Methylsulfonyl-phenyl | S—(CH₂)₈— | 7-(piperidin-1-yl-sulfonyl) | | |
| 223 | Me | 4-Methylsulfonyl-phenyl | S—(CH₂)₃— | 7-(dimethylamino-sulfonyl) | | |
| 224 | Me | 4-Methylthiazol-5-yl | S—(CH₂)₃— | 7-methoxy | | |
| 225 | Me | 2-Me-4-oxazolyl- | S—(CH₂)₃— | 7-methylsulfonyl | | |
| 226 | Me | 2,5-Di-methyl-furanyl-3- | S—(CH₂)₃— | 7-methoxy | | |
| 227 | Me | 3-Pyrrolyl | S—(CH₂)₃— | 7-cyano | | |
| 228 | Phenyl | Cyano | S—(CH₂)₃— | 7-(pyrrolidin-1-yl-sulfonyl) | | |

TABLE 1-continued

| Ex. | R¹ | R² | A | R⁶ | R⁷ | R⁸ |
|---|---|---|---|---|---|---|
| 229 | Me | Tetrazolyl- | O—(CH$_2$)$_3$— | 7-(piperidin-1-yl-sulfonyl) | | |
| 230 | Me | Phenyl- | S—(CH$_2$)$_3$— | 6-methyl | 7-cyano | |
| 231 | Et | Carboxamido | S—(CH$_2$)$_3$— | 7-cyano | | |
| 232 | Me | Pyridin-3-yl- | S—CH$_2$—C(CH$_3$)=CH—CH$_2$— | 7-(azepan-1-yl-sulfonyl) | | |
| 233 | Et | Phenyl | S—(CH$_2$)$_3$— | 6-bromo | | |
| 234 | Prop | 2-Aminothiazol-4yl- | S—(CH$_2$)$_3$— | 7-(piperidin-1-yl-sulfonyl) | | |
| 235 | Me | Pyridin-4-yl- | S—(CH$_2$)$_3$— | 7-(dimethylamino-sulfonyl) | | |
| 236 | Me | 4-Methylthiazol-5-yl | S—(CH$_2$)$_3$— | 7-cyano | | |
| 237 | cycProp | Phenyl- | S—(CH$_2$)$_3$— | 6-CH$_2$—CH$_2$—CH$_2$-7 | | |
| 238 | Me | Pyridin-3-yl- | S—CH$_2$—C(=CH$_2$)—CH$_2$ | 7-(azepan-1-yl-sulfonyl) | | |
| 239 | Et | 5-Methyl imidazol-4-yl- | S—(CH$_2$)$_{10}$— | 7-(piperidin-1-yl-sulfonyl) | | |
| 240 | Me | Methylamino | S—(CH$_2$)$_3$— | 7-nitro | | |
| 241 | Me | Pyridin-4-yl- | S—(CH$_2$)$_6$— | 7-(piperidin-1-yl-sulfonyl) | | |
| 242 | Butyl | Phenyl- | S—(CH$_2$)$_3$— | 6-methyl | 7-cyano | |
| 243 | Phenyl | 3-Pyridyl- | S—(CH$_2$)$_6$— | 7-(piperidin-1-yl-sulfonyl) | | |
| 244 | Me | Tetrazolyl- | O—(CH$_2$)$_3$— | 7-cyano | | |
| 245 | Hexyl | 3-Jodphenyl- | S—(CH$_2$)$_3$— | 6-chloro | 7-chloro | |
| 246 | Me | 4-Methylsulfonyl-phenyl | S—CH$_2$-cycProp-CH$_2$— | 7-cyano | | |
| 247 | Phenyl | tert-Butyl | S—(CH$_2$)$_3$— | 7-(pyrrolidin-1-yl-sulfonyl) | | |
| 248 | Me | tert.-Butyl | (CH$_2$)$_4$— | 6-methoxy | | |
| 249 | cycProp | tert.-Butyl | CO—(CH$_2$)$_3$— | 6-methoxy | | |
| 250 | Me | Amino- | S—(CH$_2$)$_3$— | 7-methylsulfonyl | | |
| 251 | Me | Amino- | S—(CH$_2$)$_3$— | 6-methoxy | | |
| 252 | Et | N-Methyl-2-Pyrrolyl- | S—(CH$_2$)8— | 7-cyano | | |
| 253 | Me | Methylamino- | S—(CH$_2$)$_3$— | 7-methoxy | | |
| 254 | Me | Phenyl | S—(CH$_2$)$_3$— | 8-ethenyl | | |
| 255 | Et | Phenyl | S—CH$_2$-cycHex-CH$_2$— | 7-trifluoromethoxy | | |
| 256 | Me | N-Methyl-2-Pyrrolyl- | S—CH$_2$-cycProp-CH$_2$— | 8-triflourmethyl | | |
| 257 | Prop | 3-Jod-phenyl | S—(CH$_2$)$_3$— | 7-methansulfonamid | | |
| 258 | Me | Methylamino- | S—(CH$_2$)$_3$— | 7-trifluoromethyl | | |
| 259 | Me | Tetrazolyl- | S—CH$_2$-cycHex-CH$_2$— | 7-(morpholin-1-yl-sulfonyl) | | |
| 260 | Me | Methylamino- | S—(CH$_2$)$_3$— | 7-(piperidin-1-yl-sulfonyl) | | |
| 261 | Me | N-Methyl-2-Pyrrolyl- | S—(CH$_2$)$_3$— | 7-trifluoromethyl | | |
| 262 | Me | 2-Aminothiazol-4-yl- | S—(CH$_2$)$_3$— | 7-(dimethylamino-sulfonyl) | | |
| 263 | Me | 3-Pyrrolyl | S—(CH$_2$)$_3$— | 7-methylsulfonyl | | |
| 264 | Me | 4-Imidazolyl- | S—CH$_2$—CH=CH—CH$_2$— | 7-(azepan-1-yl-sulfonyl) | | |
| 265 | Me | Propyl | (CH$_2$)$_4$— | 5-methoxy | | |
| 266 | Me | Oxadiazol-2-yl | S—(CH$_2$)$_3$— | 6-trifluoromethyl | | |
| 267 | Me | 4-Methylphenyl | O—(CH$_2$)$_3$— | 7-cyano | | |
| 268 | cycProp | Phenyl | (CH$_2$)$_4$— | 8-nitro | | |
| 269 | Me | 3-Br-Pyridin-5-yl- | S—(CH$_2$)$_3$— | 7-(piperidin-1-yl-sulfonyl) | | |
| 270 | iProp | Phenyl | S—(CH$_2$)$_3$— | 7-Acetyl | | |
| 271 | Me | 4-Methylsulfonyl-phenyl | S—(CH$_2$)$_8$— | 7-(piperidin-1-yl-sulfonyl) | | |
| 272 | Me | 3-Cyano-phenyl | S—(CH$_2$)$_3$— | 7-nitro | | |
| 273 | Me | 4-Methylthiazol-5-yl | S—(CH$_2$)$_3$— | 7-methansulfonamid | | |
| 274 | Me | 3-Cyano-phenyl | S—(CH$_2$)$_3$— | 7-cyano | | |
| 275 | Me | Oxadiazol-2-yl | S—(CH$_2$)$_3$— | 7-cyano | | |
| 276 | Me | Phenyl- | S—(CH$_2$)$_7$— | 6-methyl | | 7-(pyrolidin-1-yl-sulfonyl) |

TABLE 1-continued

| Ex. | R¹ | R² | A | R⁶ | R⁷ | R⁸ |
|---|---|---|---|---|---|---|
| 277 | Me | Phenyl- | CO—(CH$_2$)$_3$— | 7-cyano | | |
| 278 | cycProp | 4-Methoxyphenyl | (CH$_2$)$_4$— | 8-ethenyl | | |
| 279 | Me | Phenyl | S—CH$_2$—C(CH$_3$)=CH—CH$_2$— | 7-(piperidin-1-yl-sulfonyl) | | |
| 280 | Me | 6-Chloro-biphenyl-2- | S—(CH$_2$)$_3$— | 7-nitro | | |
| 281 | Me | 4-Imidazolyl- | S—(CH$_2$)$_3$— | 8-trifluoromethyl | | |
| 282 | Me | 3-Br-Pyridin-5-yl- | S—(CH$_2$)$_3$— | 7-cyano | | |
| 283 | Pentyl | 3-Pyridyl- | S—(CH$_2$)$_3$— | 6-chloro | 7-chloro | |
| 284 | Me | Pyridin-3-yl- | O—(CH$_2$)$_3$— | 7-(piperidin-1-yl-sulfonyl) | | |
| 285 | Me | 3-Pyrrolyl | S—(CH$_2$)$_3$— | 7-methoxy | | |
| 286 | Me | 2-Pyrazinyl- | O—(CH$_2$)$_3$— | 7-cyano | | |
| 287 | Et | Phenyl- | CO—(CH$_2$)$_3$— | 7-cyano | | |
| 288 | Me | 2-Me-4-Oxazolyl- | S—(CH$_2$)$_3$— | 7-(piperidin-1-yl-sulfonyl) | | |
| 289 | Me | 4-Methylsulfonyl-phenyl | S—(CH$_2$)$_3$— | 7-methylsulfonyl | | |
| 290 | Me | Phenyl | COO—(CH$_2$)$_4$— | 7-(piperidin-1-yl-sulfonyl) | | |
| 291 | Me | Oxadiazol-2-yl | S—(CH$_2$)$_3$— | 7-methylsulfonyl | | |
| 292 | Me | 2-Aminothiazol-4yl- | S—(CH$_2$)$_3$— | 7-methoxy | | |
| 293 | Me | 4-Methylphenyl | CONH—(CH$_2$)$_4$— | 7-cyano | | |
| 294 | Me | 3-Pyrrolyl | S—CH$_2$—CH=CH—CH$_2$— | 7-(piperidin-1-yl-sulfonyl) | | |
| 295 | Me | 3-Cyano-phenyl | S—(CH$_2$)$_3$— | 7-methansulfonamid | | |
| 296 | Me | 2-Pyrazinyl- | S—CH$_2$-cycProp-(CH$_2$)$_2$— | 7-(pyrolidin-1-yl-sulfonyl) | | |
| 297 | Me | Pyridin-3-yl- | S—CH$_2$—C(=CH$_2$)—CH$_2$ | 7-(piperidin-1-yl-sulfonyl) | | |
| 298 | Me | 2-Me-4-Oxazolyl- | S—(CH$_2$)$_3$— | 7-(piperidin-1-yl-sulfonyl) | | |
| 299 | Et | 3-Br-Pyridin-5-yl- | S—(CH$_2$)$_3$— | 7-cyano | | |
| 300 | Me | 6-Chloro-biphenyl-2- | S—(CH$_2$)$_3$— | 7-trifluoromethyl | | |
| 301 | iProp | Phenyl- | S—(CH$_2$)$_7$— | 6-methyl | 7-(pyrolidin-1-yl-sulfonyl) | |
| 302 | Me | 3-Benzthienyl- | S—(CH$_2$)$_3$— | 7-nitro | | |
| 303 | Me | Phenyl | CONH—(CH$_2$)$_4$— | 7-nitro | | |
| 304 | Me | Cyclohexyl- | S—(CH$_2$)$_6$— | 7-(piperidin-1-yl-sulfonyl) | | |
| 305 | Me | 3-Pyrrolyl | S—CH$_2$—CH=CH—CH$_2$— | 6-chloro | | |
| 306 | Et | 2-Pyrazinyl- | O—(CH$_2$)$_3$— | 7-(piperidin-1-yl-sulfonyl) | | |
| 307 | Me | 4-Imidazolyl- | S—(CH$_2$)$_3$— | 7-(piperidin-1-yl-sulfonyl) | | |
| 308 | Me | 3-Pyridinyl | S—(CH$_2$)$_8$— | 7-CHF$_2$ | | |
| 309 | Me | 3-Pyridyl | COO—(CH$_2$)$_3$— | 7-cyano | | |
| 310 | Me | 3-Benzthienyl- | S—(CH$_2$)$_3$— | 7-cyano | | |
| 311 | Me | 3-Pyrrolyl | S—(CH$_2$)$_3$— | 7-(piperidin-1-yl-sulfonyl) | | |
| 312 | Me | 4-Methoxyphenyl | (CH$_2$)$_2$—CH(CH$_3$)—CH$_2$—CH$_2$— | 5-hydroxy | | |
| 313 | Me | Amino- | S—(CH$_2$)$_3$— | 7-trifluoromethyl | | |
| 314 | Me | 4-Methylthiazol-5-yl | S—CH$_2$-cycProp-CH$_2$— | 7-(piperidin-1-yl-sulfonyl) | | |
| 315 | Me | Tetrazolyl- | S—(CH$_2$)$_3$— | 7-phenylsulfonyl | | |
| 316 | Me | Phenyl | S—CH$_2$-cycHex-CH$_2$— | 7-trifluoromethoxy | | |
| 317 | Phenyl | 3-Thienyl- | S—(CH$_2$)$_3$— | 7-nitro | | |
| 318 | Me | Pyridin-3-yl- | S—(CH$_2$)$_3$— | 7-(dimethylamino-sulfonyl) | | |
| 319 | Me | 4-Methylphenyl | S—CH$_2$—C(=CH$_2$)—CH$_2$ | 7-(piperidin-1-yl-sulfonyl) | | |
| 320 | Prop | 3-Benzthienyl- | S—(CH$_2$)$_3$— | 7-(dimethylamino-sulfonyl) | | |
| 321 | Me | 4-Methylthiazol-5-yl | S—(CH$_2$)$_3$— | 7-methylsulfonyl | | |

TABLE 1-continued

| Ex. | R¹ | R² | A | R⁶ | R⁷ | R⁸ |
|---|---|---|---|---|---|---|
| 322 | Me | 4-Methoxyl-phenyl | S—(CH$_2$)$_8$— | 7-(piperidin-1-yl-sulfonyl) | | |
| 323 | Me | Oxadiazol-2-yl | S—(CH$_2$)$_7$— | 7-azepan-1-yl-sulfonyl) | | |
| 324 | Me | Methylamino- | S—CH$_2$—cycProp-CH$_2$— | 7-(piperidin-1-yl-sulfonyl) | | |
| 325 | Me | 4-methoxyphenyl | S—(CH$_2$)$_3$— | 7-cyano | | |
| 326 | Butyl | 2-Aminothiazol-4yl- | S—(CH$_2$)$_3$— | 7-(piperidin-1-yl-sulfonyl) | | |
| 327 | iProp | 3-Pyrrolyl | S—CH$_2$—CH=CH—CH$_2$— | 7-(piperidin-1-yl-sulfonyl) | | |
| 328 | Me | Phenyl | CONH—(CH$_2$)$_4$— | 7-chloro | | |
| 329 | Butyl | Phenyl- | S—(CH$_2$)$_3$— | 7-(piperidin-1-yl-sulfonyl) | 8-chloro | |
| 330 | Et | 4-Imidazolyl- | S—(CH$_2$)$_3$— | 7-methoxy | | |
| 331 | Me | Phenyl | S—CH$_2$-cycProp-CH$_2$— | 6-methoxy | | |
| 332 | Me | 3-Furanyl | S—CH$_2$-cycprop-CH$_2$— | 7-(N-methylanilin-1-sulfonyl) | | |
| 333 | Me | 2-Pyrazinyl- | S—(CH$_2$)$_3$— | 7-cyano | | |
| 334 | cycProp | 2-Pyrazinyl- | O—(CH$_2$)$_3$— | 7-(piperidin-1-yl-sulfonyl) | | |
| 335 | Et | Phenyl | S—(CH$_2$)$_4$— | 7-(morpholin-1-yl-sulfonyl) | | |
| 336 | Me | Phenyl- | S—(CH$_2$)$_3$— | 7-methylsulfonyl | | |
| 337 | Me | 4-Methylphenyl | O—(CH$_2$)$_3$— | 7-(piperidin-1-yl-sulfonyl) | | |
| 338 | Butyl | Phenyl | S—(CH$_2$)$_3$— | 7-acetyl | | |
| 339 | Et | 4-Cyano-phenyl | S—CH$_2$—C(CH$_3$)=CH—CH$_2$— | 7-(piperidin-1-yl-sulfonyl) | | |
| 340 | Butyl | Phenyl- | S—(CH$_2$)$_3$— | 6-Methyl | 7-(pyrolidin-1-yl-sulfonyl) | |
| 341 | Butyl | Phenyl | S—(CH$_2$)$_3$— | 8-chloro | | |
| 342 | Et | Pyridin-3-yl | O—(CH$_2$)$_3$— | 7-(piperidin-1-yl-sulfonyl) | | |
| 343 | Me | 3-Thienyl | S—(CH$_2$)$_3$— | 7-methoxy | | |
| 344 | Me | N-Methyl-2-Pyrrolyl- | S—CH$_2$-cycHex-CH$_2$—CH$_2$— | 5-methoxy | | |
| 345 | Me | 4-Imidazolyl- | S—(CH$_2$)$_3$— | 7-methoxy | | |
| 346 | cycProp | Phenyl | CONH—(CH$_2$)$_5$— | 8-trifluoromethyl | | |
| 347 | Me | 6-Chloro-biphenyl-2- | S—(CH$_2$)$_3$— | 7-(dimethylamino-sulfonyl) | | |
| 348 | Et | 3-Pyridyl | S—(CH$_2$)$_7$— | 7-chloro | 8-chloro | |
| 349 | Me | 4-Methylsulfonylphenyl | S—CH$_2$-cycHex-CH$_2$— | 6-methoxy | | |
| 350 | Me | Methylamino- | S—(CH$_2$)$_3$— | 7-methylsulfonyl | | |
| 351 | Et | 2-Me-4-Oxazolyl- | S—(CH$_2$)$_3$— | 7-methoxy | | |
| 352 | Et | Phenyl- | S—(CH$_2$)$_3$— | 6-CH$_2$—CH$_2$—CH$_2$-7 | | |
| 353 | Et | Phenyl | S—(CH$_2$)$_4$— | 7-(pyrrolidin-1-yl-sulfonyl) | | |
| 354 | Butyl | 2-Pyrazinyl- | O—(CH$_2$)$_3$— | 7-(piperidin-1-yl-sulfonyl) | | |
| 355 | Me | 4-Methoxyl-phenyl | S—(CH$_2$)$_8$— | 7-(piperidin-1-yl-sulfonyl) | | |
| 356 | Me | Phenyl- | (CH$_2$)$_2$—CH(CH$_3$)—CH$_2$—CH$_2$— | 6-methoxy | | |
| 357 | Me | 2-Aminothiazol-4yl- | S—(CH$_2$)$_3$— | 7-trifluoromethyl | | |
| 358 | Prop | Phenyl | S—(CH$_2$)$_3$— | 7-Acetyl | | |
| 359 | Me | 4-Methylphenyl | COO—(CH$_2$)$_3$— | 7-(piperidin-1-yl-sulfonyl) | | |
| 360 | Et | 2-Me-4-Oxazolyl- | (CH$_2$)$_2$—CH(CH$_3$)—CH$_2$—CH$_2$— | 7-(morpholin-1-yl-sulfonyl) | | |
| 361 | Butyl | Carboxamido | S—(CH$_2$)$_3$— | 7-cyano | | |
| 362 | Me | Pyridin-4-yl- | S—(CH$_2$)$_3$— | 6-trifluoromethyl | | |
| 363 | Hexyl | 3-Pyridyl | S—(CH$_2$)$_3$— | 7-chloro | 8-chloro | |
| 364 | Me | N-Propyl-tetrazolyl- | S—(CH$_2$)$_3$— | 7-methylsulfonyl | | |
| 365 | Et | Phenyl- | S—CH$_2$—C(=CH$_2$)—CH$_2$ | 7-(azepan-1-yl-sulfonyl) | | |

TABLE 1-continued

| Ex. | R¹ | R² | A | R⁶ | R⁷ | R⁸ |
|---|---|---|---|---|---|---|
| 366 | cycProp | Phenyl- | $(CH_2)_4$— | 7-(3,3-dimethyl-piperidin-1-yl-sulfonyl) | | |
| 367 | Me | Phenyl | CONH—$(CH_2)_4$— | 6-chloro | 7-chloro | |
| 368 | Et | 4-Imidazolyl- | S—$CH_2$—CH=CH—$CH_2$— | 7-(azepan-1-yl-sulfonyl) | | |
| 369 | Me | Cyclohexyl- | S—$(CH_2)_3$— | 7-methoxy | | |
| 370 | Me | 2-Pyrazinyl- | S—$(CH_2)_3$— | 7-(dimethylamino-sulfonyl) | | |
| 371 | Prop | 2-Me-4-Oxazolyl- | S—$(CH_2)_3$— | 8-trifluoromethyl | | |
| 372 | Me | 2,4-Dimethoxy-phenyl | S—$CH_2$—C($CH_3$)=CH—$CH_2$— | 7-(piperidin-1-yl-sulfonyl) | | |
| 373 | Me | Cyclohexyl- | S—$(CH_2)_3$— | 7-(dimethylamino-sulfonyl) | | |
| 374 | Me | Pyridin-3-yl- | S—$(CH_2)_3$— | 7-methoxy | | |
| 375 | Me | Phenyl- | S—$(CH_2)_3$— | 7-methoxy | | |
| 376 | Me | 2-Pyrazinyl- | S—$CH_2$-cycHex-$CH_2$— | 7-(morpholin-1-yl-sulfonyl) | | |
| 377 | Me | N-Propyl-tetrazolyl- | S—$(CH_2)_3$— | 7-nitro | | |
| 378 | Me | Phenyl- | $(CH_2)_4$— | 8-triflourmethyl | | |
| 379 | Prop | 4-Methoxyphenyl | $(CH_2)_4$— | 6-ethenyl | | |
| 380 | Me | Phenyl- | S—$(CH_2)_7$— | 7-(pyrolidin-1-yl-sulfonyl) | | |
| 381 | iProp | 4-Methylthiazol-5-yl | S—$(CH_2)_3$— | 7-methylsulfonyl | | |
| 382 | iProp | Phenyl- | S—$(CH_2)_7$— | 7-(piperidin-1-yl-sulfonyl) | 8-chloro | |
| 383 | iProp | Phenyl | S—$(CH_2)_3$— | 7-carboxamid | | |
| 384 | Me | Phenyl | S—$CH_2$—C($CH_3$)=CH—$CH_2$— | 7-trifluoromethyl | | |
| 385 | Et | Phenyl | CONH—$(CH_2)_5$— | 8-trifluoromethyl | | |
| 386 | iProp | 3-Pyrrolyl | S—$(CH_2)_6$— | 7-cyano | | |
| 387 | Me | Phenyl- | S—$(CH_2)_7$— | 7-(piperidin-1-yl-sulfonyl) | 8-chloro | |
| 388 | Et | 3-Benzthienyl- | S—$(CH_2)_3$— | 7-(dimethylamino-sulfonyl) | | |
| 389 | Me | 2-Me-4-Oxazolyl- | S—$(CH_2)_3$— | 7-methoxy | | |
| 390 | Me | 2-Aminothiazol-4yl- | S—$(CH_2)_3$— | 7-nitro | | |
| 391 | Prop | 3-Br-Pyridin-5-yl- | S—$(CH_2)_3$— | 7-cyano | | |
| 392 | Me | 3-Thienyl | S—$(CH_2)_3$— | 7-nitro | | |
| 393 | Et | Phenyl | CONH—$(CH_2)_4$— | 7-chloro | | |
| 394 | Me | 4-Methylthiazol-5-yl | S—$(CH_2)_3$— | 7-nitro | | |
| 395 | Me | 2-Me-4-Oxazolyl- | S—$(CH_2)_3$— | 7-(dimethylamino-sulfonyl) | | |
| 396 | Me | 6-Chloro-biphenyl-2- | S—$(CH_2)_3$— | 7-cyano | | |
| 397 | Me | Tetrazolyl- | S—$(CH_2)_3$— | 7-(piperidin-1-yl-sulfonyl) | | |
| 398 | Me | 3-Benzthienyl- | S—$(CH_2)_3$— | 7-methylsulfonyl | | |
| 399 | Me | 3-Thienyl | S—$CH_2$—CH=CH—$CH_2$— | 7-(pyrrolidin-1-yl-sulfonyl) | | |
| 400 | Hexyl | Phenyl- | S—$(CH_2)_3$— | 6-methyl | 7-cyano | |
| 401 | Me | 3-Pyridyl | S—$(CH_2)_7$— | 6-methyl | 7-cyano | |
| 402 | Me | 2-Me-4-Oxazolyl- | S—$(CH_2)_3$— | 7-methylsulfonyl | | |
| 403 | Me | 3-Thienyl | O—$(CH_2)_3$— | 7-cyano | | |
| 404 | Prop | Phenyl- | S—$(CH_2)_3$— | 6-methyl | 7-(piperidin-1-yl-sulfonyl) | |
| 405 | Et | 2,4-Dimethoxyphenyl | S—$(CH_2)_3$— | 7-methansulfonamid | | |
| 406 | Me | Phenyl- | S—$(CH_2)_3$— | 7-trifluoromethyl | | |
| 407 | Me | 4-Methoxyphenyl | $(CH_2)_2$—CH($CH_3$)—$CH_2$—$CH_2$— | 7-(piperidin-1-yl-sulfonyl) | | |
| 408 | Me | Phenyl | S—$CH_2$-cyc-Prop-$(CH_2)_2$— | 5-methoxy | | |
| 409 | Phenyl | 3-Thienyl | $(CH_2)_4$— | 7-(piperidin-1-yl-sulfonyl) | | |
| 410 | Me | 3-Thienyl | S—$(CH_2)_3$— | 7-methansulfonamid | | |
| 411 | Me | Pyridin-3-yl- | S—$(CH_2)_3$— | 7-trifluoromethyl | | |
| 412 | Phenyl | tert-Butyl | O—$(CH_2)_3$— | 7-(pyrrolidin-1-yl-sulfonyl) | | |

TABLE 1-continued

| Ex. | R¹ | R² | A | R⁶ | R⁷ | R⁸ |
|---|---|---|---|---|---|---|
| 413 | Me | 3-Pyrrolyl | S—(CH$_2$)$_3$— | 7-trifluoromethyl | | |
| 414 | Me | N-Methyl-2-Pyrrolyl- | S—(CH$_2$)$_3$— | 7-nitro | | |
| 415 | iProp | Phenyl | S—(CH$_2$)$_3$— | 8-trifluoromethyl | | |
| 416 | Butyl | 3-Thienyl | S—(CH$_2$)$_8$— | 7-(pyrrolidin-1-yl-sulfonyl) | | |
| 417 | Me | Phenyl- | S—CH$_2$—C(=CH$_2$)—CH$_2$ | 7-(piperidin-1-yl-sulfonyl) | | |
| 418 | Me | 2-Me-4-Oxazolyl- | S—(CH$_2$)$_3$— | 7-nitro | | |
| 419 | Me | 2-Aminothiazol-4yl- | S—(CH$_2$)$_3$— | 7-phenylsulfonyl | | |
| 420 | Me | 4-Methylthiazol-5-yl | O—(CH$_2$)$_3$— | 7-cyano | | |
| 421 | Me | 4-Methylsulfonylphenyl | S—(CH$_2$)$_3$— | 7-trifluoromethyl | | |
| 422 | Me | 4-methylsulfonylphenyl | O—(CH$_2$)$_3$— | 7-(piperidin-1-yl-sulfonyl) | | |
| 423 | Butyl | 3-Pyridyl- | S—(CH$_2$)$_3$— | 7-chloro | 8-chloro | |
| 424 | Me | Methylamino- | S—CH$_2$—C(CH$_3$)=CH—CH$_2$— | 7-(piperidin-1-yl-sulfonyl) | | |
| 425 | Me | Carboxamido | S—(CH$_2$)$_3$— | 7-cyano | | |
| 426 | Me | 4-Methoxyphenyl | S—(CH$_2$)$_3$— | 7-phenylsulfonyl | | |
| 427 | Et | 3-Pyrrolyl | S—CH$_2$—CH=CH—CH$_2$— | 7-(piperidin-1-yl-sulfonyl) | | |
| 428 | Me | 3-Cyano-phenyl | S—(CH$_2$)$_3$— | 7-trifluoromethyl | | |
| 429 | Me | 5-Methyl imidazol-4-yl- | S—(CH$_2$)$_3$— | 7-cyano | | |
| 430 | Prop | N-Propyl-tetrazolyl- | S—(CH$_2$)$_3$— | 7-cyano | | |
| 431 | Me | 2,5-Di-methyl-furanyl-3- | S—(CH$_2$)$_3$— | 7-(dimethylamino-sulfonyl) | | |
| 432 | Prop | Pyridin-3-yl- | S—CH$_2$—C(=CH$_2$)—CH$_2$ | 7-(azepan-1-yl-sulfonyl) | | |
| 433 | Me | 4-Methylsulfonylphenyl | S—(CH$_2$)$_3$— | 7-(piperidin-1-yl-sulfonyl) | | |
| 434 | Butyl | Phenyl | (CH$_2$)$_4$— | 8-nitro | | |
| 435 | Me | 4-Methylphenyl | COO—(CH$_2$)$_4$— | 7-(piperidin-1-yl-sulfonyl) | | |
| 436 | Me | 3-Furanyl | S—CH$_2$-cycHex-CH$_2$—CH$_2$— | 7-phenylsulfonyl | | |
| 437 | Me | 3-Jod-phenyl | S—(CH$_2$)$_3$— | 7-trifluoromethyl | | |
| 438 | Et | 2-Pyrazinyl- | O—(CH$_2$)$_3$— | 8-ethenyl | | |
| 439 | Me | 3-Benzthienyl- | S—(CH$_2$)$_3$— | 7-(piperidin-1-yl-sulfonyl) | | |
| 440 | Me | Cyclohexyl- | S—(CH$_2$)$_3$— | 7-(piperidin-1-yl-sulfonyl) | | |
| 441 | Me | Pyridin-3-yl- | S—CH$_2$-cycHex-CH$_2$— | 6-methoxy | | |
| 442 | Me | 2-Me-4-Oxazolyl- | S—(CH$_2$)$_3$— | 7-nitro | | |
| 443 | Me | 2-Pyrazinyl- | (CH$_2$)$_4$— | 7-(morpholin-1-yl-sulfonyl) | | |
| 444 | Prop | 2-Pyrazinyl- | S—(CH$_2$)$_3$— | 8-ethenyl | | |
| 445 | Me | 4-Methoxyphenyl | S—(CH$_2$)$_3$— | 7-trifluoromethyl | | |
| 446 | Me | 4-Imidazolyl- | S—(CH$_2$)$_3$— | 7-methylsulfonyl | | |
| 447 | Me | Phenyl- | S—(CH$_2$)$_7$— | 7-(pyrolidin-1-yl-sulfonyl) | | |
| 448 | Me | Cyclohexyl- | S—(CH$_2$)$_3$— | 7-trifluoromethyl | | |
| 449 | Butyl | Phenyl- | (CH$_2$)$_4$— | 7-(3,3-dimethyl-piperidin-1-yl-sulfonyl) | | |
| 450 | Et | Phenyl | S—(CH$_2$)$_3$— | 8-ethenyl | | |
| 451 | Me | 4-Methoxyphenyl | S—(CH$_2$)$_3$— | 7-(piperidin-1-yl-sulfonyl) | | |
| 452 | iProp | Phenyl | S—(CH$_2$)$_4$— | 7-(morpholin-1-yl-sulfonyl) | | |
| 453 | Me | Cyano | S—(CH$_2$)$_8$— | 6,7-dimethoxy | | |
| 454 | Me | 2-Aminothiazol-4yl- | S—CH$_2$—CH=CH—CH$_2$— | 7-(piperidin-1-yl-sulfonyl) | | |
| 455 | Et | Phenyl | COO—(CH$_2$)$_3$— | 7-(piperidin-1-yl-sulfonyl) | | |

TABLE 1-continued $$\text{Structure with } R^1, R^2, A, R^6, R^7, R^8 \text{ substituents on triazole-tetrahydroisoquinoline scaffold}$$

| Ex. | R¹ | R² | A | R⁶ | R⁷ | R⁸ |
|---|---|---|---|---|---|---|
| 456 | Me | 3-Cyano-phenyl | S—(CH₂)₃— | 7-methylsulfonyl | | |
| 457 | Me | 2-Pyrazinyl- | S—(CH₂)₃— | 7-nitro | | |
| 458 | Me | 3-Cyano-phenyl | S—CH₂—C(=CH₂)—CH₂ | 7-(piperidin-1-yl-sulfonyl) | | |
| 459 | cycProp | N-Methyl-2-Pyrrolyl- | S—(CH₂)₈— | 7-cyano | | |
| 460 | Me | 4-Methoxyphenyl | S—(CH₂)₃— | 7-nitro | | |
| 461 | Me | Oxadiazol-2-yl | S—(CH₂)₃— | 7-(piperidin-1-yl-sulfonyl) | | |
| 462 | Me | Tetrazolyl- | S—(CH₂)₇— | 7-(piperidin-1-yl-sulfonyl) | | |
| 463 | Butyl | Phenyl | (CH₂)₄— | 7-(pyrrolidin-1-yl-sulfonyl) | | |
| 464 | Prop | 4-Methylphenyl | S—CH₂—C(=CH₂)—CH₂ | 7 piperidin-1-yl-sulfonyl) | | |
| 465 | Me | Phenyl- | S—(CH₂)₃— | 6-CH₂—CH₂—CH₂-7 | | |
| 466 | Me | N-Methyl-2-Pyrrolyl- | S—(CH₂)₃— | 7-methylsulfonyl | | |
| 467 | Me | 3-Thienyl | S—(CH₂)₃— | 7-trifluoromethyl | | |
| 468 | Et | Cyano | S—(CH₂)₈— | 6-methoxy | 7-methoxy | |
| 469 | cycProp | Phenyl- | S—(CH₂)₃— | 6-CH(CH₃)CH₂—NH-7 | | |
| 470 | Me | 3-Br-Pyridin-5-yl- | S—(CH₂)₃— | 7-methylsulfonyl | | |
| 471 | Me | Phenyl- | S—(CH₂)₃— | 6-CH(CH₃)CH₂—N(CH₃)-7 | | |
| 472 | Et | 4-Methoxyphenyl | (CH₂)₄— | 8-ethenyl | | |
| 473 | Me | Tetrazolyl- | S—(CH₂)₃— | 7-trifluoromethyl | | |
| 474 | Me | 6-Chloro-biphenyl-2- | S—(CH₂)₃— | 7-methoxy | | |
| 475 | Me | 4-Pyridyl- | (CH₂)₄— | 7-(pyrolidin-1-yl-sulfonyl) | | |
| 476 | cycProp | Phenyl | CONH—(CH₂)₄— | 6-chloro | 7-chloro | |
| 477 | Me | 2-Me-4-Oxazolyl- | S—(CH₂)₆— | 7-nitro | | |
| 478 | Me | 2-Me-4-Oxazolyl- | S—(CH₂)₃— | 7-methoxy | | |
| 479 | Me | 4-Methoxyphenyl | S—CH₂—CH=CH—CH₂— | 7-(piperidin-1-yl-sulfonyl) | | |
| 480 | Me | Cyano | S—(CH₂)₈— | 6-methoxy | 7-methoxy | |
| 481 | Me | tert.-Butyl | CO—(CH₂)₃ | 6-methoxy | | |
| 482 | Et | 3-Cyano-phenyl | S—(CH₂)₃— | 7-methansulfonamid | | |
| 483 | Prop | Cyano | S—(CH₂)₈— | 6-methoxy | 7-methoxy | |
| 484 | Me | 3-Pyrrolyl | S—CH₂-cycHex-CH₂—CH₂— | 7-cyano | | |
| 485 | Me | Methylamino- | S—(CH₂)₃— | 7-(dimethylamino-sulfonyl) | | |
| 486 | Me | 2,5-Di-methyl-furanyl-3- | S—(CH₂)₃— | 7-(piperidin-1-yl-sulfonyl) | | |
| 487 | Me | 2,5-Dimethyl-furanyl-3- | S—(CH₂)₃— | 7-nitro | | |
| 488 | iProp | 4-Methoxyphenyl | (CH₂)₄— | 8-ethenyl | | |
| 489 | Et | Tetrazolyl- | S—(CH₂)₃— | 7-nitro | | |
| 490 | Me | Phenyl | COO—(CH₂)₃— | 7-(piperidin-1-yl-sulfonyl) | | |
| 491 | Me | 4-Imidazolyl- | S—(CH₂)₃— | 7-nitro | | |
| 492 | Me | 3-Thienyl | O—(CH₂)₃— | 7-(piperidin-1-yl-sulfonyl) | | |
| 493 | Et | Phenyl | S—CH₂—C(CH₃)=CH—CH₂— | 8-trifluoromethyl | | |
| 494 | Me | Pyridin-4-yl- | S—(CH₂)₆— | 7-nitro | | |
| 495 | Me | N-Methyl-2-Pyrrolyl- | S—(CH₂)₃— | 7-methansulfonamid | | |
| 496 | Et | Phenyl- | S—(CH₂)₃— | 6-methyl | 7-cyano | |
| 497 | Prop | 4-Methylthiazol-5-yl | S—(CH₂)₃— | 7-trifluoromethyl | | |
| 498 | Me | Phenyl | O—(CH₂)₃— | 7-(piperidin-1-yl-sulfonyl) | | |
| 499 | Me | 4-Cyano-phenyl | S—CH₂—C(CH₃)=CH—CH₂— | 7-(piperidin-1-yl-sulfonyl) | | |
| 500 | Et | Phenyl | S—(CH₂)₃— | 7-Carboxamid | | |
| 501 | Me | N-Propyl-tetrazolyl- | S—(CH₂)₃— | 7-(piperidin-1-yl-sulfonyl) | | |

TABLE 1-continued

| Ex. | R¹ | R² | A | R⁶ | R⁷ | R⁸ |
|---|---|---|---|---|---|---|
| 502 | Me | Amino- | S—(CH$_2$)$_3$— | 7-(dimethylaminosulfonyl) | | |
| 503 | Me | 2,4-Dimethoxy-phenyl | S—(CH$_2$)$_3$— | 7-(piperidin-1-yl-sulfonyl) | | |
| 504 | Me | 3-Benzthienyl- | CO-(CH$_2$)$_3$— | 7-phenylsulfonyl | | |
| 505 | Me | 4-Imidazolyl- | S—(CH$_2$)$_3$— | 7-cyano | | |
| 506 | Et | Phenyl | S—CH$_2$-cycHex-CH$_2$—CH$_2$— | 5-methoxy | | |
| 507 | Et | 3-Pyrrolyl | S—(CH$_2$)$_6$— | 7-cyano | | |
| 508 | Me | 3-Pyrrolyl | S—(CH$_2$)$_3$— | 7-methansulfonamid | | |
| 509 | Me | Tetrazolyl- | S—(CH$_2$)$_7$— | 7-(piperidin-1-yl-sulfonyl) | | |
| 510 | Me | Tetrazolyl- | S—(CH$_2$)$_3$— | 7-methansulfonamid | | |
| 511 | Me | 3-Thienyl | COO—(CH$_2$)$_4$— | 7-(piperidin-1-yl-sulfonyl) | | |
| 512 | Et | 2-Me-4-Oxazolyl- | S—(CH$_2$)$_3$— | 7-(piperidin-1-yl-sulfonyl) | | |
| 513 | Me | Pyridin-4-yl- | S—(CH$_2$)$_3$— | 7-methylsulfonyl | | |
| 514 | Butyl | N-Methyl-2-Pyrrolyl- | S—(CH$_2$)$_8$— | 7-cyano | | |
| 515 | Me | Phenyl- | S—(CH$_2$)$_3$— | 6-CH(CH$_3$)CH$_2$—NH-7 | | |
| 516 | Me | Pyridin-4-yl- | S—(CH$_2$)$_3$— | 7-cyano | | |
| 517 | Me | 3-Thienyl | S—CH$_2$-cyc-Prop-(CH$_2$)$_2$— | 7-(3,3-dimethyl-piperidin-1-yl-sulfonyl) | | |
| 518 | Me | 2,4-Dimethoxyphenyl | O—(CH$_2$)$_3$— | 7-cyano | | |
| 519 | Me | 4-Methylsulfonyl-phenyl | O—(CH$_2$)$_3$— | 7-cyano | | |
| 520 | Me | 4-Methylthiazol-5-yl | S—CH$_2$—C(=CH$_2$)—CH$_2$ | 7-(azepan-1-yl-sulfonyl) | | |
| 521 | Me | Amino- | S—(CH$_2$)$_3$— | 7-(piperidin-1-yl-sulfonyl) | | |
| 522 | Prop | N-Methyl-2-Pyrrolyl- | S—(CH$_2$)$_8$— | 7-cyano | | |
| 523 | Me | 5-Methyl imidazol-4-yl- | S—(CH$_2$)$_3$— | 7-trifluoromethyl | | |
| 524 | Me | Cyclohexyl- | S—(CH$_2$)$_3$— | 7-methylsulfonyl | | |
| 525 | Et | Pyridin-3-yl- | S—CH$_2$—C(=CH$_2$)—CH$_2$ | 7-(azepan-1-yl-sulfonyl) | | |
| 526 | Prop | Phenyl | S—(CH$_2$)$_3$— | 8-ethenyl | | |
| 527 | Me | 5-Methyl imidazol-4-yl- | S—CH$_2$—C(CH$_3$)=CH—CH$_2$— | 7-(pyrrolidin-1-yl-sulfonyl) | | |
| 528 | Me | Tetrazolyl- | S—CH$_2$-cycProp-CH$_2$— | 6-methoxy | | |
| 529 | Me | Phenyl | S—CH$_2$—C(=CH$_2$)—CH$_2$ | 7-(azepan-1-yl-sulfonyl) | | |
| 530 | Me | 6-Chloro-biphenyl-2- | S—(CH$_2$)$_3$— | 7-(piperidin-1-yl-sulfonyl) | | |
| 531 | Et | Phenyl- | S—(CH$_2$)$_7$— | 6-methyl | 7-(pyrolidin-1-yl-sulfonyl) | |
| 532 | Me | Pyridin-3-yl- | S—(CH$_2$)$_3$— | 7-methansulfonamid | | |
| 533 | Me | 2-Pyrazinyl- | S—CH$_2$—C(=CH$_2$)—CH$_2$ | 7-(piperidin-1-yl-sulfonyl) | | |
| 534 | Et | 3-Jod-phenyl | O—(CH$_2$)$_3$— | 7-cyano | | |
| 535 | Me | 3-Benzthienyl- | S—(CH$_2$)$_3$— | 6-methoxy | | |
| 536 | Me | Oxadiazol-2-yl | S—(CH$_2$)$_3$— | 7-methoxy | | |
| 537 | Me | 6-Chloro-biphenyl-2- | S—CH$_2$—C(CH$_3$)=CH—CH$_2$— | 7-(piperidin-1-yl-sulfonyl) | | |
| 538 | cycProp | 4-Methylthiazol-5-yl | S—CH$_2$—C(=CH$_2$)—CH$_2$ | 7-(azepan-1-yl-sulfonyl) | | |
| 539 | Me | Pyridin-3-yl- | S—(CH$_2$)$_3$— | 7-(piperidin-1-yl-sulfonyl) | | |
| 540 | Et | 4-Methylthiazol-5-yl | S—(CH$_2$)$_3$— | 7-trifluoromethyl | | |
| 541 | Me | 3-Pyrrolyl | S—(CH$_2$)$_3$— | 7-(dimethylamino-sulfonyl) | | |
| 542 | Me | 3-Pyridyl | COO—(CH$_2$)$_4$— | 7-(piperidin-1-yl-sulfonyl) | | |
| 543 | Prop | Carboxamido | S—(CH$_2$)$_3$— | 7-cyano | | |
| 544 | Me | 4-Jod-phenyl | COO—(CH$_2$)$_3$— | 7-cyano | | |
| 545 | Hexyl | Phenyl- | (CH$_2$)$_4$— | 7-(3,3-dimethyl-piperidin-1-yl-sulfonyl) | | |

TABLE 1-continued

| Ex. | R$^1$ | R$^2$ | A | R$^6$ | R$^7$ | R$^8$ |
|---|---|---|---|---|---|---|
| 546 | Me | 2-Me-4-Oxazolyl- | S—(CH$_2$)$_3$— | 7-trifluoromethyl | | |
| 547 | Et | Phenyl- | S—(CH$_2$)$_7$— | 7-(piperidin-1-yl-sulfonyl) | 8-chloro | |
| 548 | Prop | Phenyl | S—(CH$_2$)$_4$— | 7-(pyrrolidin-1-yl-sulfonyl) | | |
| 549 | Me | N-Propyl-tetrazolyl- | S—(CH$_2$)$_3$— | 7-methoxy | | |
| 550 | Me | 2-Pyrazinyl- | S—(CH$_2$)$_3$— | 7-methylsulfonyl | | |
| 551 | Me | Phenyl | S—CH$_2$—C(CH$_3$)=CH—CH$_2$— | 8-trifluoromethyl | | |
| 552 | Butyl | tert.-Butyl | CO—(CH$_2$)$_3$— | 6-methoxy | | |
| 553 | Prop | 5-Methyl imidazol-4-yl- | S—(CH$_2$)$_{10}$— | 7-(piperidin-1-yl-sulfonyl) | | |
| 554 | Me | 4-Jod-phenyl | S—(CH$_2$)$_3$— | 7-cyano | | |
| 555 | Me | 5-Methyl imidazol-4-yl- | S—(CH$_2$)$_3$— | 7-(dimethylamino-sulfonyl) | | |
| 556 | Me | 3-Benzthienyl- | (CH$_2$)$_4$— | 7-phenylsulfonyl | | |
| 557 | Me | Pyridin-3-yl- | O—(CH$_2$)$_3$— | 7-cyano | | |
| 558 | Me | Tetrazolyl- | S—(CH$_2$)$_3$— | 7-nitro | | |
| 559 | Me | 3-Benzthienyl- | S—(CH$_2$)$_6$— | 7-(pyrolidin-1-yl-sulfonyl) | | |
| 560 | cycProp | Phenyl | S—(CH$_2$)$_3$— | 7-Acetyl | | |
| 561 | iProp | Phenyl | S—(CH$_2$)$_4$— | 7-(pyrrolidin-1-yl-sulfonyl) | | |
| 562 | Me | Phenyl- | S—(CH$_2$)$_3$— | 7-(piperidin-1-yl-sulfonyl) | | |
| 563 | Me | 2-Me-4-Oxazolyl- | S—(CH$_2$)$_3$— | 7-cyano | | |
| 564 | Me | 5-Methyl imidazol-4-yl- | S—(CH$_2$)$_3$— | 7-methoxy | | |
| 565 | Prop | Phenyl- | S—(CH$_2$)$_3$— | 6-CH(CH$_3$)CH$_2$—N(CH$_3$)-7 | | |
| 566 | Me | N-Propyl-tetrazolyl- | S—(CH$_2$)$_3$— | 7-trifluoromethyl | | |
| 567 | Me | 2,5-Di-methyl-furanyl-3- | S—(CH$_2$)$_3$— | 7-trifluoromethyl | | |
| 568 | Me | Phenyl | O—(CH$_2$)$_3$— | 7-cyano | | |
| 569 | Me | 4-Jod-phenyl | S—(CH$_2$)$_3$— | 7-nitro | | |
| 570 | Me | N-Methyl-2-Pyrrolyl- | S—(CH$_2$)$_3$— | 7-cyano | | |
| 571 | Prop | 3-Pyridyl | S—(CH$_2$)$_7$— | 6-methyl | 7-cyano | |
| 572 | Me | 2,5-Di-methyl-furanyl-3- | S—(CH$_2$)$_3$— | 7-cyano | | |
| 573 | Me | 2-Pyrazinyl- | S—(CH$_2$)$_3$— | 7-methansulfonamid | | |
| 574 | Me | 2-Me-4-Oxazolyl- | S—(CH$_2$)$_3$— | 7-cyano | | |
| 575 | Et | Phenyl | O—(CH$_2$)$_3$— | 7-cyano | | |
| 576 | Me | Methylamino- | S—(CH$_2$)$_3$— | 7-methansulfonamid | | |
| 577 | Me | 3-Thienyl | S—(CH$_2$)$_3$— | 7-cyano | | |
| 578 | Me | 2-Chloro-phenyl | (CH$_2$)$_4$— | 7-trifluoromethoxy | | |
| 579 | Butyl | 3-Pyrrolyl | S—CH$_2$—CH=CH—CH$_2$— | 7-(piperidin-1-yl-sulfonyl) | | |
| 580 | cycProp | 3-Cyano-phenyl | S—(CH$_2$)$_3$— | 7-methansulfonamid | | |
| 581 | Me | N-Propyl-tetrazolyl- | S—(CH$_2$)$_3$— | 7-(dimethylamino-sulfonyl) | | |
| 582 | Me | 4-Methylphenyl | COO—(CH$_2$)$_4$— | 7-trifluoromethyl | | |
| 583 | Me | 5-Methyl imidazol-4-yl- | S—(CH$_2$)$_3$— | 7-methylsulfonyl | | |
| 584 | Me | 3-Br-Pyridin-5-yl- | S—(CH$_2$)$_3$— | 7-methoxy | | |
| 585 | Me | 3-Thienyl | S—CH$_2$-cycHex-CH$_2$— | 7-trifluoromethoxy | | |
| 586 | Me | Pyridin-3-yl- | S—(CH$_2$)$_3$— | 7-nitro | | |
| 587 | Et | 3-Thienyl | COO—(CH$_2$)$_3$— | 7-(piperidin-1-yl-sulfonyl) | | |
| 588 | Prop | 3-Thienyl | S—(CH$_2$)$_3$— | 7-(dimethylaminosulfonyl) | | |
| 589 | Butyl | 3-Br-Pyridin-5-yl- | S—(CH$_2$)$_3$— | 7-cyano | | |

TABLE 1-continued

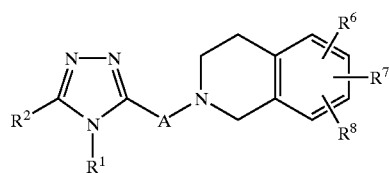

| Ex. | R¹ | R² | A | R⁶ | R⁷ | R⁸ |
|---|---|---|---|---|---|---|
| 590 | Me | Pyridin-3-yl- | S—(CH$_2$)$_3$— | 7-cyano | | |
| 591 | Et | 3-Cyano-phenyl | S—(CH$_2$)$_3$— | 7-nitro | | |
| 592 | Prop | Phenyl | S—(CH$_2$)$_{10}$— | 7-Carboxamid | | |
| 593 | Et | 3-Furanyl | S—CH$_2$-cycHex-CH$_2$—CH$_2$— | 7-phenylsulfonyl | | |
| 594 | Me | N-Methyl-2-Pyrrolyl- | S—(CH$_2$)$_3$— | 7-methoxy | | |
| 595 | Me | 3-Cyano-phenyl | S—CH$_2$-cycHex-CH$_2$—CH$_2$— | 6-Methyl | | |
| 596 | Me | 4-Methylsulfonyl-phenyl | S—(CH$_2$)$_3$— | 7-methansulfonamid | | |
| 597 | Me | 2-Aminothiazol-4yl- | S—(CH$_2$)$_3$— | 7-(piperidin-1-yl-sulfonyl) | | |
| 598 | Prop | Phenyl | S—(CH$_2$)$_3$— | 6-bromo | | |
| 599 | Prop | 4-Methylthiazol-5-yl | S—(CH$_2$)$_3$— | 7-methylsulfonyl | | |
| 600 | Me | 2,4-Dimethoxyphenyl | O—(CH$_2$)$_3$— | 7-(piperidin-1-yl-sulfonyl) | | |
| 601 | Et | Pyridin-4-yl | S—(CH$_2$)$_3$— | 7-nitro | | |
| 602 | Me | N-Methyl-2-Pyrrolyl- | S—CH$_2$—C(CH$_3$)=CH—CH$_2$— | 7-(piperidin-1-yl-sulfonyl) | | |
| 603 | Me | 3-Br-Pyridin-5-yl- | S—(CH$_2$)$_6$— | 7-(piperidin-1-yl-sulfonyl) | | |
| 604 | iProp | Phenyl- | S—(CH$_2$)$_3$— | 6-methyl | 7-cyano | |
| 605 | Et | 2-Pyrazinyl- | CO—(CH$_2$)$_3$— | 7-(morpholin-1-yl-sulfonyl) | | |
| 606 | Me | Phenyl- | S—(CH$_2$)$_3$— | 6-methyl | 7-nitro | |
| 607 | Butyl | 4-Methylthiazol-5-yl | S—CH$_2$—C(=CH$_2$)—CH$_2$ | 7-(azepan-1-yl-sulfonyl) | | |
| 608 | Me | 4-Methoxyphenyl | S—(CH$_2$)$_3$— | 7-(dimethylamino-sulfonyl) | | |
| 609 | Me | 3-Br-Pyridin-5-yl- | S—(CH$_2$)$_6$— | 7-(piperidin-1-yl-sulfonyl) | | |
| 610 | Me | Pyridin-4-yl | S—(CH$_2$)$_3$— | 7-methoxy | | |
| 611 | cycProp | Pyridin-3-yl- | O—(CH$_2$)$_3$— | 7-(piperidin-1-yl-sulfonyl) | | |
| 612 | Me | 3-Br-Pyridin-5-yl- | S—(CH$_2$)$_3$— | 7-trifluoromethyl | | |
| 613 | Me | 2-Me-4-Oxazolyl- | S—(CH$_2$)$_3$— | 8-trifluoromethyl | | |
| 614 | Prop | Phenyl | S—(CH$_2$)$_3$— | 8-trifluoromethyl | | |
| 615 | Me | 3-Benzthienyl- | S—(CH$_2$)$_3$— | 7-trifluoromethyl | | |
| 616 | Et | Phenyl | S—(CH$_2$)$_3$— | 7-acetyl | | |
| 617 | Me | Pyridin-3-yl | S—CH$_2$-cycProp-CH$_2$— | 7-(pyrolidin-1-yl-sulfonyl) | | |
| 618 | Me | Oxadiazol-2-yl | S—(CH$_2$)$_7$— | 7-(piperidin-1-yl-sulfonyl) | | |
| 619 | Phenyl | 3-Thienyl | S—(CH$_2$)$_3$— | 7-cyano | | |
| 620 | Me | 3-Jod-phenyl | O—(CH$_2$)$_3$— | 7-cyano | | |
| 621 | Me | Phenyl | CONH—(CH$_2$)$_4$— | 6-methoxy | | 8-methyl |
| 622 | Me | 3-Thienyl | S—(CH$_2$)$_3$— | 6-CH(CH$_3$)CH$_2$—NH-7 | | 5-methyl |
| 623 | Me | 3-Thienyl | S—(CH$_2$)$_3$— | 6-CH$_2$—CH$_2$—CH$_2$—CH$_2$-7 | | 8-bromo |
| 624 | Me | 4-Pyridyl | S—(CH$_2$)$_3$— | 6-CH$_2$—CH$_2$—CH$_2$-7 | | 8-ethenyl |
| 625 | Me | 3-Pyridyl- | S—(CH$_2$)$_3$— | 5-methoxy | 7-chloro | 8-chloro |
| 626 | Me | 3-Phenyl- | O—(CH$_2$)$_3$— | 6-chloro | 7-chloro | 8-methyl |

If no meaning is given, R⁷ and R⁸ are hydrogen.
Here and in the following tables is:
Me=methyl
Et=ethyl
cycProp=cyclopropyl
Prop=n-propyl
iProp=isopropyl
cycHex=cyclohexyl The following compounds can be prepared in an analogous way in principle:

TABLE 2

| Ex. | R¹ | R² | A | R⁶ |
|---|---|---|---|---|
| 627 | Me | Phenyl | CONH—(CH$_2$)4— | 5-nitro |
| 628 | Butyl | Methylamino | S—(CH$_2$)$_3$— | 5-fluoro |
| 629 | Me | Oxadiazol-2-yl | S—(CH$_2$)$_7$— | 5-(piperidin-1-yl-sulfonyl) |
| 630 | Me | Tetrazolyl- | S—(CH$_2$)$_7$— | 5-(piperidin-1-yl-sulfonyl) |
| 631 | Me | 3-Cyano-phenyl | S—(CH$_2$)$_3$— | 5-fluoro |
| 632 | Et | 3-Thienyl | S—(CH$_2$)$_3$— | 5-methoxy |
| 633 | Me | Carboxamid | S—CH$_2$—C(CH$_3$)=CH—CH$_2$— | 5-methoxy |
| 634 | Butyl | Cyclohexyl- | S—CH$_2$—cycProp-(CH2)$_2$— | 5-chloro |
| 635 | Me | 3-Pyrrolyl | S—(CH$_2$)$_3$— | 5-nitro |
| 636 | Me | 2-Pyrazinyl- | S—(CH$_2$)$_3$— | 5-nitro |
| 637 | Pentyl | tert.-Butyl | CO—(CH$_2$)$_3$— | 6-methoxy |
| 638 | Me | Pyridin-3-yl- | CO—(CH$_2$)$_3$— | 5-fluoro |
| 639 | Me | 4-Jod-phenyl | S—(CH$_2$)$_3$— | 5-fluoro |
| 640 | Me | 4-Methylsulfonyl-phenyl | S—(CH$_2$)$_8$— | 5-(piperidin-1-yl-sulfonyl) |
| 641 | iProp | N-Propyl-tetrazolyl- | S—(CH$_2$)$_3$— | 5-fluoro |
| 642 | cycProp | tert.-Butyl | CO—(CH$_2$)$_3$— | 6-methoxy |
| 643 | Me | 2-Aminothiazol-4yl- | S—(CH$_2$)$_3$— | 5-fluoro |
| 644 | cycProp | 4-Methylsulfonyl-phenyl | S—(CH$_2$)$_8$— | 5-(piperidin-1-yl-sulfonyl) |
| 645 | Me | Pyridin-3-yl- | S—CH$_2$—CH=CH—CH$_2$— | 5-methoxy |
| 646 | Me | N-Propyl-tetrazolyl- | S—CH$_2$—CH=CH—CH$_2$— | 5-nitro |
| 647 | cycProp | Carboxamido | S—(CH$_2$)$_3$— | 5-fluoro |
| 648 | Me | N-Methyl-2-Pyrrolyl- | S—(CH$_2$)$_3$— | 5-nitro |
| 649 | Me | 2-Me-4-Oxazolyl- | S—(CH$_2$)$_3$— | 5-nitro |
| 650 | Me | Pyridin-4-yl- | S—(CH$_2$)$_3$— | 5-nitro |
| 651 | Me | 3-Br-Pyridin-5-yl- | S—CH$_2$—CH=CH—CH$_2$— | 5-methoxy |
| 652 | Me | Phenyl- | S—(CH$_2$)$_3$— | 5-fluoro |
| 653 | Me | 4-Jod-phenyl | S—(CH$_2$)$_3$— | 5-methoxy |
| 654 | Me | 3-Pyrrolyl | S—(CH$_2$)$_3$— | 5-methoxy |
| 655 | Me | Phenyl- | S—CH$_2$—CH=CH—CH$_2$— | 5-(piperidin-1-yl-sulfonyl) |
| 656 | Me | 3-Cyano-phenyl | S—(CH$_2$)$_3$— | 5-methoxy |
| 657 | Me | N-Methyl-2-Pyrrolyl- | S—CH$_2$-cycProp-(CH2)$_2$— | 5-methoxy |
| 658 | Me | Phenyl | O—(CH$_2$)$_3$— | 5-cyano |
| 659 | Pentyl | Cyclohexyl- | S—(CH$_2$)$_3$— | 5-chloro |
| 660 | Me | 3-Benzthienyl- | S—CH$_2$-cycProp-(CH$_2$)$_2$— | 5-fluoro |
| 661 | Pentyl | Carboxamido | S—(CH$_2$)$_3$— | 5-chloro |
| 662 | Et | 5-Methyl imidazol-4-yl- | S—CH$_2$—CH=CH—CH$_2$— | 5-methoxy |
| 663 | iProp | Cyclohexyl- | S—(CH$_2$)$_3$— | 5-fluoro |
| 664 | Me | 3-Benzthienyl- | S—(CH$_2$)$_3$— | 5-nitro |
| 665 | Butyl | Cyclohexyl- | S—CH$_2$—cycProp-(CH$_2$)$_2$— | 5-methoxy |
| 666 | Me | 4-Methoxyphenyl | S—(CH$_2$)$_3$— | 5-methoxy |
| 667 | Prop | N-Propyl-tetrazolyl- | S—CH$_2$—CH=CH—CH$_2$— | 5-fluoro |
| 668 | Pentyl | Phenyl | CONH—(CH$_2$)$_4$— | 5-cyano |
| 669 | Me | Phenyl- | CO—(CH$_2$)$_3$— | 5-methoxy |
| 670 | Prop | Cyclohexyl- | S—(CH$_2$)$_3$— | 5-fluoro |
| 671 | Butyl | Methylamino | S—(CH$_2$)$_3$— | 5-methoxy |
| 672 | Me | 4-Methylthiazol-5-yl- | S—(CH$_2$)$_3$— | 5-cyano |
| 673 | cycProp | N-Propyl-tetrazolyl- | S—CH$_2$—CH=CH—CH$_2$— | 5-nitro |
| 674 | cycProp | Propyl | CO—(CH$_2$)$_3$— | 5-methoxy |
| 675 | Me | Oxadiazol-2-yl | S—CH$_2$—CH=CH—CH$_2$— | 5-nitro |
| 676 | Me | 3-Pyridyl | S—(CH$_2$)$_7$— | 5-chloro |
| 677 | Me | 5-Methyl imidazol-4-yl- | S—(CH$_2$)$_3$— | 5-fluoro |
| 678 | Me | 5-Methyl imidazol-4-yl- | S—CH$_2$—C(CH$_3$)=CH—CH$_2$— | 5-(pyrrolidin-1-yl-sulfonyl) |
| 679 | Me | 3-Pyrrolyl | S—(CH$_2$)$_3$— | 5-fluoro |
| 680 | Me | Cyclohexyl- | O-(CH$_2$)$_3$— | 5-nitro |
| 681 | Me | Methylamino- | S—CH$_2$—C(CH$_3$)=CH—CH$_2$— | 5-(piperidin-1-yl-sulfonyl) |
| 682 | iProp | 6-Chloro-biphenyl-2- | S—(CH$_2$)$_3$— | 5-fluoro |
| 683 | Me | 3-Cyano-phenyl | S—(CH$_2$)$_3$— | 5-nitro |
| 684 | Pentyl | N-Propyl-tetrazolyl- | S—CH$_2$—CH=CH—CH$_2$— | 5-chloro |
| 685 | Me | Phenyl | CONH—(CH$_2$)$_4$— | 5-cyano |
| 686 | cycProp | Phenyl | COO—(CH$_2$)$_3$— | 5-(piperidin-1-yl-sulfonyl) |
| 687 | Me | Amino | S—(CH$_2$)$_3$— | 5-nitro |
| 688 | Me | Phenyl | CONH—(CH$_2$)$_4$— | 5-chloro |
| 689 | Me | 2-Pyrazinyl- | S—(CH$_2$)$_3$— | 5-fluoro |
| 690 | Me | 4-Jod-phenyl | S—CH$_2$—CH=CH—CH$_2$— | 5-nitro |
| 691 | Me | 2-Pyrazinyl- | S—CH$_2$-cycProp-(CH$_2$)$_2$— | 5-(pyrolidin-1-yl-sulfonyl) |
| 692 | Me | Pyridin-4-yl- | S—(CH$_2$)$_3$— | 5-methoxy |
| 693 | Pentyl | 4-Methylsulfonyl-phenyl | S—(CH$_2$)$_8$— | 5-(piperidin-1-yl-sulfonyl) |
| 694 | Pentyl | N-Methyl-2-Pyrrolyl- | S—(CH$_2$)$_3$— | 5-chloro |
| 695 | cycProp | Phenyl | O—(CH$_2$)$_3$— | 5-cyano |

TABLE 2-continued

| Ex. | R¹ | R² | A | R⁶ |
|---|---|---|---|---|
| 696 | Me | 4-Imidazolyl- | S—(CH$_2$)$_3$— | 5-nitro |
| 697 | Me | 3-Pyrrolyl | S—CH$_2$—CH═CH—CH$_2$— | 6-chloro |
| 698 | Me | Oxadiazol-2-yl | (CH2)$_2$—CH(CH$_3$)—CH$_2$—CH$_2$— | 5-fluoro |
| 699 | Me | 6-Chloro-biphenyl-2- | S—(CH$_2$)$_3$— | 5-nitro |
| 700 | Butyl | 4-Methoxyphenyl | S—(CH$_2$)$_3$— | 5-methoxy |
| 701 | Me | 3-Br-Pyridin-5-yl- | S—(CH$_2$)$_3$— | 5-nitro |
| 702 | Prop | N-Propyl-tetrazolyl- | S—CH$_2$—CH═CH—CH$_2$— | 5-chloro |
| 703 | Me | 5-Methyl imidazol-4-yl- | (CH$_2$)$_2$—CH(CH$_3$)—CH$_2$—CH$_2$— | tert-Butyl |
| 704 | Pentyl | Carboxamido | S—(CH$_2$)$_3$— | 5-fluoro |
| 705 | Me | 2-Pyrazinyl- | S—(CH$_2$)$_3$— | 5-methoxy |
| 706 | Pentyl | Phenyl- | CO—(CH$_2$)$_3$— | 6-methoxy |
| 707 | Me | 4-Imidazolyl- | S—(CH$_2$)$_3$— | 5-methoxy |
| 708 | Me | Phenyl- | CO—(CH$_2$)$_3$— | 6-methoxy |
| 709 | Me | Tetrazolyl- | S—CH$_2$—C(═CH$_2$)—CH$_2$ | 5-nitro |
| 710 | cycProp | N-Methyl-2-Pyrrolyl- | S—(CH$_2$)$_3$— | 5-chloro |
| 711 | cycProp | Cyclohexyl- | S—(CH$_2$)$_3$— | 5-nitro |
| 712 | cycProp | Carboxamido | S—(CH$_2$)$_3$— | 5-chloro |
| 713 | iProp | 2,5-Di-methyl-furanyl-3- | S—(CH$_2$)$_3$— | 5-fluoro |
| 714 | Me | Amino | S—CH$_2$-cycProp-(CH$_2$)$_2$— | 5-fluoro |
| 715 | Me | 3-Thienyl | (CH$_2$)$_2$—CH(CH$_3$)—CH$_2$—CH$_2$— | 5-fluoro |
| 716 | Me | 3-Thienyl | O—(CH$_2$)$_3$— | 5-nitro |
| 717 | Me | tert.-Butyl | CO—(CH$_2$)$_3$— | 6-methoxy |
| 718 | Me | Amino | S—(CH$_2$)$_3$— | 5-methoxy |
| 719 | Me | 2-Me-4-Oxazolyl- | S—(CH$_2$)$_3$— | 5-fluoro |
| 720 | Et | Tetrazolyl- | S—CH$_2$—C(CH$_3$)═CH—CH$_2$— | 5-methoxy |
| 721 | Prop | Carboxamido | S—(CH$_2$)$_3$— | 5-chloro |
| 722 | Et | 4-Methylthiazol-5-yl | S—(CH$_2$)$_3$— | 5-methoxy |
| 723 | Me | 4-Imidazolyl- | S—(CH$_2$)$_3$— | 5-fluoro |
| 724 | Me | 4-Methylthiazol-5-yl | S—(CH$_2$)$_3$— | 5-fluoro |
| 725 | Et | 2-Me-4-Oxazolyl- | S—(CH$_2$)$_3$— | 5-methoxy |
| 726 | Butyl | 4-Methoxyphenyl | S—(CH$_2$)$_3$— | 5-fluoro |
| 727 | Me | 2,5-Di-methyl-furanyl-3- | S—(CH$_2$)$_3$— | 5-methoxy |
| 728 | Me | 3-Br-Pyridin-5-yl- | S—(CH$_2$)$_3$— | 5-fluoro |
| 729 | Pentyl | N-Methyl-2-Pyrrolyl- | S—(CH$_2$)$_3$— | 5-fluoro |
| 730 | cycProp | N-Methyl-2-Pyrrolyl- | S—(CH$_2$)$_3$— | 5-nitro |
| 731 | Prop | Cyclohexyl- | S—(CH$_2$)$_3$— | 5-chloro |
| 732 | cycProp | 3-Pyridyl | S—(CH$_2$)$_7$— | 5-chloro |
| 733 | cycProp | Cyclohexyl- | S—(CH$_2$)$_3$— | 5-chloro |
| 734 | Me | N-Propyl-tetrazolyl- | S—(CH$_2$)$_3$— | 5-methoxy |
| 735 | Me | Methylamino | S—(CH$_2$)$_3$— | 5-nitro |
| 736 | Me | Pyridin-3-yl- | S—(CH$_2$)$_3$— | 5-nitro |
| 737 | Me | 2-Aminothiazol-4yl- | S—(CH$_2$)$_3$— | 5-nitro |
| 738 | Et | Oxadiazol-2-yl | S—(CH$_2$)$_3$— | 5-methoxy |
| 739 | Me | 3-Cyano-phenyl | S—CH$_2$—C(═CH$_2$)—CH$_2$ | 5-(piperidin-1-yl-sulfonyl) |
| 740 | cycProp | Phenyl- | CO—(CH$_2$)$_3$— | 6-methoxy |
| 741 | Me | 2-Me-4-Oxazolyl- | (CH$_2$)$_2$—CH(CH$_3$)—CH$_2$—CH$_2$— | 5-(morpholin-1-yl-sulfonyl) |
| 742 | Et | 2-Aminothiazol-4yl- | S—CH$_2$—CH═CH—CH$_2$— | 5-methoxy |
| 743 | Me | 2,5-Di-methyl-furanyl-3- | S—(CH$_2$)$_3$— | 5-nitro |
| 744 | Me | Phenyl | COO—(CH$_2$)$_3$— | 5-(piperidin-1-yl-sulfonyl) |
| 745 | Me | 2-Me-4-Oxazolyl- | S—(CH$_2$)$_3$— | 5-fluoro |
| 746 | iProp | Pyridin-4-yl- | S—(CH$_2$)$_3$— | 5-fluoro |
| 747 | Me | Methylamino | S—CH$_2$-cycProp-(CH$_2$)$_2$— | 5-methoxy |
| 748 | Me | 5-Methyl imidazol-4-yl- | S—(CH$_2$)$_3$— | 5-nitro |
| 749 | Me | 2-Me-4-Oxazolyl- | S—(CH$_2$)$_3$— | 5-cyano |
| 750 | cycProp | Carboxamido | S—(CH$_2$)$_3$— | 5-cyano |
| 751 | Me | Tetrazolyl- | S—(CH$_2$)$_3$— | 5-fluoro |
| 752 | Pentyl | Cyclohexyl- | S—(CH$_2$)$_3$— | 5-fluoro |
| 753 | Prop | N-Methyl-2-Pyrrolyl- | S—(CH$_2$)$_3$— | 5-chloro |
| 754 | Me | N-Methyl-2-Pyrrolyl- | S—(CH$_2$)$_3$— | 5-fluoro |
| 755 | cycProp | N-Propyl-tetrazolyl- | S—CH$_2$—CH═CH—CH$_2$— | 5,6-dichloro |
| 756 | Pentyl | Propyl | CO—(CH$_2$)$_3$— | 5-methoxy |
| 757 | Me | 4-Methoxyphenyl | S—(CH$_2$)$_3$— | 5-nitro |
| 758 | Me | Propyl | CO—(CH$_2$)$_3$— | 5-methoxy |
| 759 | Me | 2-Me-4-Oxazolyl- | S—(CH$_2$)$_3$— | 5-methoxy |
| 760 | cycProp | Phenyl | CONH—(CH$_2$)$_4$— | 5-cyano |
| 761 | Me | Carboxamido | S—(CH$_2$)$_3$— | 5-cyano |
| 762 | Et | tert.Butyl | S—CH$_2$-cycProp-(CH$_2$)$_2$— | 5-methoxy |
| 763 | cycProp | N-Methyl-2-Pyrrolyl- | S—(CH$_2$)$_3$— | 5-fluoro |

Examples of Pharmaceutical Administration Forms

A) Tablets

Tablets of the following composition were pressed on a tabletting machine in the customary manner

- 40 mg of the substance from Example 1
- 120 mg of corn starch
- 13.5 mg of gelatin
- 45 mg of lactose
- 2.25 mg of Aerosil® (chemically pure silicic acid in a submicroscopically fine dispersion)
- 6.75 mg of potato starch (as a 6% paste)

B) Sugar-coated tablets

- 20 mg of the substance from Example 3
- 60 mg of core composition
- 70 mg of sugar-coating composition The core composition consists of 9 parts of corn starch, 3 parts of lactose and 1 part of vinylpyrrolidone-vinyl acetate 60:40 copolymer. The sugar-coating composition consists of 5 parts of cane sugar, 2 parts of corn starch, 2 parts of calcium carbonate and 1 part of talc. The sugar-coated tablets which have been prepared in this way are then provided with an enteric coating.

Biological Investigations—Receptor Binding Studies $D_3$ binding test

Cloned human $D_3$-receptor-expressing CCL 1,3 mouse fibroblasts, obtainable from Res. Biochemicals Internat. One Strathmore Rd., Natick, Mass. 01760-2418 USA, were used for the binding studies.

Cell Preparation

The $D_3$-expressing cells were multiplied in RPMI-1640 containing 10% fetal calf serum (GIBCO No. 041-32400 N); 100 U of penicillin/ml and 0.2% streptomycin (GIBO BRL, Gaithersburg, Md., USA). After 48 h, the cells were washed with PBS and incubated for 5 min with 0.05% trypsin-containing PBS. After that, the solution was neutralized with medium and the cells were collected by centrifuging at 300 g. In order to lyse the cells, the pellet was washed briefly with lysis buffer (5 mM Tris-HCl, pH 7.4, containing 10% glycerol) and after that incubated, at 4° C. for 30 min, at a concentration of $10^7$ cells/ml of lysis buffer. The cells were centrifuged at 200 g for 10 min and the pellet was stored in liquid nitrogen.

Binding Tests

For the $D_3$-receptor binding test, the membranes were suspended in incubation buffer (50 mM Tris-HCl, pH 7.4, containing 120 mM NaCl, 5 mM KCl, 2 mM CaCl$_2$, 2 mM MgCl$_2$, 10 μM quinolinol, 0.1% ascorbic acid and 0.1% BSA), at a concentration of approx. $10^6$ cells/250 μl of test mixture, and incubated at 30° C. with 0.1 nM $^{125}$iodosulpiride in the presence and absence of the test substance. The nonspecific binding was determined using $10^{-6}$ M spiperone.

After 60 min, the free radioligand and the bound radioligand were separated by filtering through GF/B glass fiber filters (Whatman, England) on a Skatron cell harvester (Skatron, Lier, Norway), and the filters were washed with ice-cold Tris-HCl buffer, pH 7.4. The radioactivity which had collected on the filters was quantified using a Packard 2200 CA liquid scintillation counter.

The $K_i$ values were determined by means of nonlinear regression analysis using the LIGAND program.

2) $D_2$ binding test

Cell Culture

HEK-293 cells possessing stably expressed human dopamine D2A receptors were cultured in RPMI 1640 containing Glutamix I™ and 25 mM HEPES containing 10% fetal calf serum albumin. All the media contained 100 units of penicillin per mol and 100 μg/ml of streptomycin/ml. The cells were maintained at 37° C. in a moist atmosphere containing 5% CO$_2$.

The cells were prepared for the binding studies by trypsinizing them (0.05% solution of trypsin) at room temperature for 3–5 minutes. After that, the cells were centrifuged at 250 g for 10 minutes and treated with lysis buffer (5 mM Tris-HCl, 10% glycerol, pH 7.4) at 4° C. for 30 minutes. After centrifuging at 250 g for 10 minutes, the residue was stored at −20° C. until used.

Receptor Binding Tests

Low affinity state dopamine $D_2$ receptor using $^{125}$I-spiperone (81 TBq/mmol, Du Pont de Nemours, Dreieich)

The test mixtures (1 ml) consisted of $1\times10^5$ cells in incubation buffer (50 mM Tris, 120 mM NaCl, 5 mM KCl, 2 mM MgCl$_2$ and 2 mM CaCl$_2$, pH 7.4 with HCl) and 0.1 mM $^{125}$I-spiperone (total binding) or additionally 1 μM haloperidol (nonspecific binding) or test substance.

After the test mixtures had been incubated at 25° C. for 60 minutes, they were filtered through GM/B glass filters (Whatman, England) on a Skatron cell harvester (from Zinsser, Frankfurt), and the filters were washed with ice-cold 50 mM Tris-HCl buffer, pH 7.4. The radioactivity which had collected on the filters was quantified using a Packard 2200 CA liquid scintillation counter.

The results were evaluated as described in a).

The $K_i$ values were determined by way of nonlinear regression analysis using the LIGAND program or by converting the IC$_{50}$ values using the Cheng and Prusoff formula.

In these tests, the compounds according to the invention exhibit very good affinities for the $D_3$ receptor (<1 μmolar, in particular <100 nmolar) and bond selectively to the $D_3$ receptor.

In table 3 $pK_i(D_3)$ values (negative logarithm of the affinity constant for the $D_3$ receptor) and selectivity versus $D_2$ receptor $(K_i(D_2)/K_i(D_3))$ are given for the compounds of the examples 3, 4 and 7.

TABLE 3

| Example | pK$_i$ (D$_3$) | Selectivity |
| --- | --- | --- |
| 3 | 8,02 | 78 |
| 4 | 7,96 | 67 |
| 7 | 8,37 | 81 |

We claim:

1. A triazole compound of the formula I

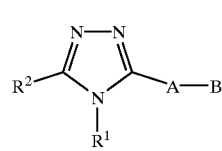

where $R^1$ is H, $C_1$–$C_6$-alkyl, which may be substituted by OH, $OC_1$–$C_6$-alkyl, halogen or phenyl, $C_3$–$C_6$-cycloalkyl or phenyl;

$R^2$ is H, $C_1$–$C_6$-alkyl, which may be substituted by OH, $OC_1$–$C_6$-alkyl, halogen or phenyl, $C_1$–$C_6$-alkoxy, $C_1$–$C_6$-alkylthio, $C_2$–$C_6$-alkenyl, $C_2$–$C_6$-alkynyl, $C_3$–$C_6$-cycloalkyl, halogen, CN, COOR$^3$, CONR$^3$R$^4$, NR$^3$R$^4$, SO$_2$R$^3$, SO$_2$NR$^3$R$^4$ or an aromatic radical which is selected from phenyl, naphthyl and a 5- or 6-membered heterocyclic radical having 1, 2, 3 or 4 heteroatoms which are selected, independently of each other, from O, N and S, with it being possible for the aromatic radical to have one or two substituents which are selected, independently of each other, from $C_1$–$C_6$-alkyl, which may be substituted by OH, OC$_1$–C$_6$-alkyl, halogen or phenyl, $C_1$–$C_6$-alkoxy, $C_2$–$C_6$-alkenyl, $C_2$–$C_6$-alkynyl, $C_3$–$C_6$-cycloalkyl, halogen, CN, COR$^3$, NR$^3$R$^4$, NO$_2$, SO$_2$R$^3$, SO$_2$NR$^3$R$^4$ and phenyl which may be substituted by one or two radicals which are selected, independently of each other, from $C_1$–$C_6$-alkyl, $C_1$–$C_6$-alkoxy, NR$^3$R$^4$, CN, CF$_3$, CHF$_2$ or halogen;

R$^3$ and R$^4$ are, independently of each other, H, $C_1$–$C_6$-alkyl, which may be substituted by OH, OC$_1$–C$_6$-alkyl, halogen or phenyl, or phenyl;

A is $C_4$–$C_{10}$-alkylene or $C_3$–$C_{10}$-alkylene which comprises at least one group Z which is selected from O, S, CONR$^3$, COO, CO, $C_3$–$C_6$-cycloalkyl and a double or triple bond;

B is a radical of the following formula:

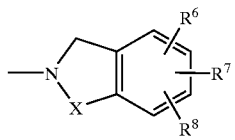

where

X is CH$_2$ or CH$_2$CH$_2$;

R$^6$, R$^7$ and R$^8$ are, independently of each other, selected from H, $C_1$–$C_6$-alkyl, which may be substituted by OH, OC$_1$–C$_6$-alkyl, which may be substituted by amino, mono- or di-$C_1$–$C_4$-alkylamino; $C_1$–$C_6$-alkylthio, halogen or phenyl; OH, $C_1$–$C_6$-alkoxy, OCF$_3$, OSO$_2$CF$_3$, SH, $C_1$–$C_6$-alkylthio, $C_2$–$C_6$-alkenyl, $C_2$–$C_6$-alkynyl, halogen, CN, NO$_2$, C(O)CH$_3$, CO$_2$R$^3$, SO$_2$R$^3$, SO$_2$NR$^3$R$^4$, where R$^3$ and R$^4$ have the abovementioned meanings and may also form together with the N atom to which they are bonded a saturated or unsaturated heterocycle with 5 to 7 ring atoms and 1 or 2 N heteroatoms, CONR$^3$R$^4$, NHSO$_2$R$^3$, NR$^3$R$^4$, a 5- or 6-membered carbocyclic, aromatic or nonaromatic ring and a 5- or 6-membered heterocyclic, aromatic or nonaromatic ring with 1 or 2 heteroatoms which are selected, independently of each other, from O, N and S, with the carbocyclic or heterocyclic ring being able to have one or two substituents which are selected, independently of each other, from $C_1$–$C_6$-alkyl, phenyl, phenoxy, halogen, $C_1$–$C_6$-alkoxy, OH, NO$_2$, CF$_3$ and CHF$_2$, and with two of the substituents R$^6$, R$^7$ and R$^8$ being able to form, together with the carbon atoms of the phenyl ring to which they are bonded, a phenyl, cyclopentyl or cyclohexyl ring which is fused to the phenyl ring, with the possibility for one or two of the CH or CH$_2$ groups in the fused ring being replaced by a nitrogen atom, an NH or an N—$C_1$–$C_6$ alkyl group; or a salt thereof with a physiologically tolerated acid.

2. A compound as claimed in claim 1 of the formula I, where A is $C_4$–$C_{10}$-alkylene or $C_3$–$C_{10}$-alkylene which comprises at least one group Z which is selected from O, S, COO, CO, a double bond or triple bond and $C_3$–$C_6$-cycloalkyl.

3. A compound as claimed in claim 1 of the formula I, where A is $C_4$–$C_{10}$-alkylene or $C_3$–$C_{10}$-alkylene which comprises at least one group Z which is selected from O, S, a double bond and cyclohexyl.

4. A compound as claimed in claim 1 of the formula I, where R$^2$ is an aromatic radical which is unsubstituted or has one or two substituents which are selected, independently of each other, from $C_1$–$C_6$-alkyl, OH, $C_1$–$C_6$-alkoxy, phenyl, CN and halogen.

5. A compound as claimed in claim 1 of the formula I, where R$^2$ is H, $C_1$–$C_6$-alkyl, phenyl, thienyl, furanyl, tetrazolyl, pyrrolyl, pyridyl or pyrazinyl.

6. A compound as claimed in claim 1 of the formula I, where R$^1$ is H, $C_1$–$C_6$-alkyl or $C_3$–$C_6$-cycloalkyl.

7. A compound as claimed in claim 1 of the formula I, where R$^6$, R$^7$ and R$^8$ are selected, independently of each other, from H, $C_1$–$C_6$-alkyl, OH, $C_1$–$C_6$-alkoxy, $C_1$–$C_6$-akylthio-$C_1$–$C_6$-alkyl, halogen, CN, C(O)CH$_3$, NO$_2$, SO$_2$R$^3$, SO$_2$NR$^3$R$^4$ and CONR$^3$R$^4$.

8. A compound as claimed in claim 1 of the formula I, where

R$^1$ is H, $C_1$–$C_6$-alkyl or phenyl,

R$^2$ is H, $C_1$–$C_6$-alkyl, phenyl, thienyl, furanyl, tetrazolyl, pyrrolyl, thiazolyl or pyrazinyl, A is —SC$_3$—$C_{10}$-alkylene which may comprise a double bond, and R$^6$, R$^7$ and R$^8$ are selected from H, $C_1$–$C_6$-alkyl, $C_1$–$C_6$-alkoxy, halogen, SO$_2$NR$^3$R$^4$, CN, C(O)CH$_3$, NO$_2$, CF$_3$, CONR$^3$R$^4$, CHF$_2$, OSO$_2$CF$_3$, OCF$_3$ and NHSO$_2$—$C_1$–$C_6$-alkyl.

9. A pharmaceutical which comprises at least one compound as claimed in claim 1, optionally together with physiologically acceptable excipients and/or adjuvants.

10. A triazole compound of formula I

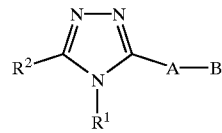

(I)

where

R$^1$ is H, $C_1$–$C_6$-alkyl, which may be substituted by OH, OC$_1$–C$_6$-alkyl, halogen or phenyl, $C_3$–$C_6$-cycloalkyl or phenyl;

R$^2$ is H, $C_1$–$C_6$-alkyl, which may be substituted by OH, OC$_1$–C$_6$-alkyl, halogen or phenyl, $C_1$–$C_6$-alkoxy, $C_1$–$C_6$-alkylthio, $C_2$–$C_6$-alkenyl, $C_2$–$C_6$-alkynyl, $C_3$–$C_6$-cycloalkyl, halogen, CN, COOR$^3$, CONR$^3$R$^4$, NR$^3$R$^4$, SO$_2$R$^3$, SO$_2$NR$^3$R$^4$ or an aromatic radical which is selected from phenyl, naphthyl and a 5- or 6-membered heterocyclic radical having 1, 2, 3 or 4 heteroatoms which are selected, independently of each other, from O, N and S, with it being possible for the aromatic radical to have one or two substituents which are selected, independently of each other, from $C_1$–$C_6$-alkyl, which may be substituted by OH, OC$_1$–C$_6$-alkyl, halogen or phenyl, $C_1$–$C_6$-alkoxy, $C_2$–$C_6$-alkenyl, $C_2$–$C_6$-alkynyl, $C_3$–$C_6$-cycloalkyl, halogen, CN, COR$^3$, NR$^3$R$^4$, NO$_2$, SO$_2$R$^3$, SO$_2$NR$^3$R$^4$ and phenyl which may be substituted by one or two radicals which are selected, independently of each other, from $C_1$–$C_6$-alkyl, $C_1$–$C_6$-alkoxy, NR$^3$R$^4$, CN, CF$_3$, CHF$_2$ or halogen;

R$^3$ and R$^4$ are, independently of each other, H, $C_1$–$C_6$-alkyl, which may be substituted by OH, OC$_1$–C$_6$-alkyl, halogen or phenyl, or phenyl;

A is $C_4$–$C_{10}$-alkylene or $C_3$–$C_{10}$-alkylene which comprises at least one group Z which is selected from O, S, $CONR^3$, COO, CO, $C_3$–$C_6$-cycloalkyl and a double or triple bond;

B is a radical of the following formula:

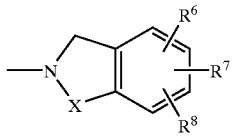

where

X is $CH_2CH_2$;

$R^6$, $R^7$ and $R^8$ are, independently of each other, selected from H, $C_1$–$C_6$-alkyl, which may be substituted by OH, $OC_1$–$C_6$-alkyl, which may be substituted by amino, mono- or di-$C_1$–$C_4$-alkylamino; $C_1$–$C_6$-alkylthio, halogen or phenyl; OH, $C_1$–$C_6$-alkoxy, $OCF_3$, $OSO_2CF_3$, SH, $C_1$–$C_6$-alkylthio, $C_2$–$C_6$-alkenyl, $C_2$–$C_6$-alkynyl, halogen, CN, $NO_2$, $C(O)CH_3$, $CO_2R^3$, $SO_2R^3$, $SO_2NR^3R^4$, where $R^3$ and $R^4$ have the abovementioned meanings and may also form together with the N atom to which they are bonded a saturated or unsaturated heterocycle with 5 to 7 ring atoms and 1 or 2 N heteroatoms, $CONR^3R^4$, $NHSO_2R^3$, $NR^3R^4$, a 5- or 6-membered carbocyclic, aromatic or nonaromatic ring and a 5- or 6-membered heterocyclic, aromatic or nonaromatic ring with 1 or 2 heteroatoms which are selected, independently of each other, from O, N and S, with the carbocyclic or heterocyclic ring being able to have one or two substituents which are selected, independently of each other, from $C_1$–$C_6$-alkyl, phenyl, phenoxy, halogen, $C_1$–$C_6$-alkoxy, OH, $NO_2$, $CF_3$ and $CHF_2$, and with two of the substituents $R^6$, $R^7$ and $R^8$ being able to form, together with the carbon atoms of the phenyl ring to which they are bonded, a phenyl, cyclopentyl or cyclohexyl ring which is fused to the phenyl ring, with the possibility for one or two of the CH or $CH_2$ groups in the fused ring being replaced by a nitrogen atom, an NH or an N—$C_1$–$C_6$ alkyl group; or a salt thereof with a physiologically tolerated acid.

11. The compound defined in claim 10, wherein A is $C_4$–$C_{10}$-alkylene or $C_3$–$C_{10}$-alkylene which comprises at least one group Z selected from the group consisting of O, S, COO, CO, a double bond, a triple bond and $C_3$–$C_6$-cycloalkyl.

12. The compound defined in claim 10, wherein A is $C_4$–$C_{10}$-alkylene or $C_3$–$C_{10}$-alkylene which comprises at least one group Z selected from the group consisting of O, S, a double bond and cyclohexyl.

13. The compound defined in claim 10, wherein $R^2$ is an aromatic radical which is unsubstituted or has one or two substituents which are selected, independently of each other, from $C_1$–$C_6$-alkyl, OH, $C_1$–$C_6$-alkoxy, phenyl, CN and halogen.

14. The compound defined in claim 10, wherein $R^2$ is H, $C_1$–$C_6$-alkyl, phenyl, thienyl, furanyl, tetrazolyl, pyrrolyl, pyridyl or pyrazinyl.

15. The compound defined in claim 10, wherein $R^1$ is H, $C_1$–$C_6$-alkyl or $C_3$–$C_6$-cycloalkyl.

16. The compound defined in claim 10, wherein $R^6$, $R^7$ and $R^8$ are selected, independently of each other, from H, $C_1$–$C_6$-alkyl, OH, $C_1$–$C_6$-alkoxy, $C_1$–$C_6$-akylthio-$C_1$–$C_6$-alkyl, halogen, CN, $C(O)CH_3$, $NO_2$, $SO_2R^3$, $SO_2NR^3R^4$ and $CONR^3R^4$.

17. The compound defined in claim 10, wherein $R^1$ is H, $C_1$–$C_6$-alkyl or phenyl, $R^2$ is H, $C_1$–$C_6$-alkyl, phenyl, thienyl, furanyl, tetrazolyl, pyrrolyl, thiazolyl or pyrazinyl, A is —$SC_3$–$C_{10}$-alkylene which may comprise a double bond, and $R^6$, $R^7$ and $R^8$ are selected from H, $C_1$–$C_6$-alkyl, $C_1$–$C_6$-alkoxy, halogen, $SO_2NR^3R^4$, CN, $C(O)CH_3$, $NO_2$, $CF_3$, $CONR^3R^4$, $CHF_2$, $OSO_2CF_3$, $OCF_3$ and $NHSO_2$—$C_1$–$C_6$-alkyl.

18. A pharmaceutical which comprises at least one compound as defined in claim 10, optionally together with physiologically acceptable excipients and/or adjuvants.

* * * * *